United States Patent
Burke et al.

(10) Patent No.: US 6,291,676 B1
(45) Date of Patent: Sep. 18, 2001

(54) WATER-SOLUBLE DERIVATIVES OF CAMPTOTHECIN/HOMOCAMPTOTHECIN

(75) Inventors: Thomas G. Burke, Lexington, KY (US); Ayhan S. Demir, Neunkirchen; Cihangir Tanyeli, Ankara, both of (TR); Ashok J. Chavan, Lexington, KY (US); Tie-Lin Wang, San Diego, CA (US); Yves Pommier, Bethesda, MD (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/517,210

(22) Filed: Mar. 2, 2000

Related U.S. Application Data

(60) Provisional application No. 60/122,621, filed on Mar. 3, 1999.

(51) Int. Cl.[7] .................................................. C07D 491/22
(52) U.S. Cl. .............................................................. 546/48
(58) Field of Search ........................................ 546/41, 48

(56) References Cited

U.S. PATENT DOCUMENTS

| | | | |
|---|---|---|---|
| Re. 32,518 | 10/1987 | Miyaasaka et al. ................... | 546/48 |
| 5,342,947 | 8/1994 | Lackey et al. ......................... | 546/41 |
| 5,446,047 | 8/1995 | Danishefsky et al. ............... | 514/280 |
| 5,525,731 | 6/1996 | Danishefsky et al. ................. | 546/48 |
| 5,552,156 | 9/1996 | Burke .................................... | 424/450 |

FOREIGN PATENT DOCUMENTS

WO 98/28305 * 7/1998 (FR).

OTHER PUBLICATIONS

Jew et al., Biorg. Med. Chem. Letters vol. 6,7, pp. 845–848, 1996.*

Wang et al. (Bioorg. Med. Chem., 2(12), 1397–402), 1994.*

Wang et al. (Bioorg. Med. Chem., 4(4), 579–82), 1994.*

Sawada et al. (Chem. Pharm. Bull., 39(10), 2574–80), 1991.*

\* cited by examiner

*Primary Examiner*—Bruck Kifle
(74) *Attorney, Agent, or Firm*—King and Schikli, PLLC

(57) ABSTRACT

Camptothecin and homocamptothecin analogs and derivatives are provided incorporating alkylamine and polyalkylamine moieties.

2 Claims, 11 Drawing Sheets

WATER-SOLUBLE DERIVATIVES OF CAMPTOTHECIN/HOMOCAMPTOTHECIN

This application claims the benefit of U.S. Provisional Patent Application No. 60/122,621 filed March 3, 1999.

This invention was made with U.S. Government support under Grant Number NIH CA 63653 awarded by the National Institutes of Health. In addition to its existing rights, the United States of America may have additional rights to this invention under the above grant.

TECHNICAL FIELD

The present invention relates to water-soluble camptothecin and homocamptothecin compounds. More particularly, the invention relates to C-7 substituted camptothecin derivatives prepared by C-7 haloalkylation, Hydroalkylation and aminoalkylation of camptothecin or its C-12 substituted 7-membered E-ring analog 5-ethyl-5-hydroxy-1,4,5,13-tetrahydro-3H,15H-oxepino[3',4':6,7]indolizino-[1,2-b]quinoline-3,15-dione (homocamptothecin) derivatives prepared by C-12 haloalkylation, hydroalkylation and aminoalkylation of homocamptothecin to form water-soluble camptothecin/homocamptothecin compounds.

BACKGROUND OF THE INVENTION

Camptothecin, a plant alkaloid isolated from trees indigenous to China, and analogs thereof such as 9-aminocamptothecin, 9-nitrocamptothecin, 10-hydroxycamptothecin, 10,11-methylenedioxycamptothecin, 9-nitro-10,11-methylenedioxycamptothecin, 9-chloro-10,11-methylenedioxycamptothecin, 9-amino-10,11-methylenedioxycamptothecin, 7-ethyl-10-hydroxycamptothecin (SN-38), topotecan, DX-8951, Lurtotecan (GI147221C), and other analogs (collectively referred to herein as camptothecin drugs) are presently under study worldwide in research laboratories and cancer clinics. In lab tests and in clinical trials, these camptothecin drugs have aroused considerable interest as a result of their ability to halt the growth of a wide range of human tumors. For example, these drugs exhibit unprecedented high levels of antitumor activities against human colon cancer [Giovanella, et al. *Science* 246: 1046–1048 (Washington, D.C.) (1989)]. Camptothecin drugs have also been shown to be effective against other experimental cancer types such as lung, breast, and malignant melanoma.

Camptothecin drugs are thought to inhibit the proliferation of cancer cells by interfering with the breakage/reunion reaction of the enzyme topoisomerase I, a nuclear enzyme implicated in DNA replication and RNA transcription. A camptothecin drug stabilizes and forms a reversible enzyme-camptothecin-DNA ternary complex, designated the cleavage complex. The formation of the cleavable complex specifically prevents the reunion step of the breakage/union cycle of the topoisomerase reaction. Topoisomerase I inhibitors are also known to be useful in the treatment of HIV.

Camptothecin and homocamptothecin both contain five-membered ring systems as shown below.

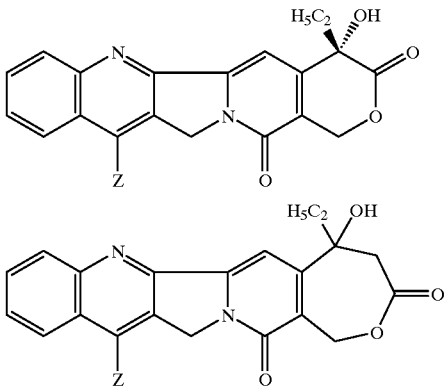

For both camptothecin (top structure) and homocamptothecin (bottom structure), Z=hydrogen. Unfortunately, camptothecin/homocamptothecin and many structurally-related camptothecin analogs/derivatives are water-insoluble. This water insolubility makes administration of camptothecin drugs difficult. In an effort to address this problem a number of synthetic efforts have been directed to derivatizing the A-ring and/or B-ring to improve water-solubility while maintaining cytotoxic activity.

To date, some water-soluble camptothecin derivatives have been prepared by derivatizing the A and B rings and by opening the lactone E-ring. See, for example, U.S. Pat. Nos. 5,646,159, 5,559,235, 5,670,500, 5,663,177, 5,677,286, and 5,734,056. U.S. Pat. No. 5,646,159 discloses water-soluble pro-drug type camptothecin compounds, in which the 20-position hydroxyl group is esterified. Enzymes present within the body can break the ester bond after injection to form the parent camptothecin compound.

U.S. Pat. No. 5,559,235 discloses water-soluble camptothecin compounds, in which the A ring has 10,11-ethylene or methylenedioxy rings and substituents at C-7. U.S. Pat. No. 5,670,500 discloses water-soluble camptothecin drugs, in which the A ring is connected to the substituted furan-ring. U.S. Pat. No. 5,663,177 discloses water-soluble camptothecin analogs, in which the A- and B rings are connected with a heterocyclic ring containing nitrogen. U.S. Pat. No. 5,677,286 discloses water-soluble camptothecin analogs in which the A ring has non-ionic sugar moieties, which increase the water solubility. U.S. Pat. No. 5,734,056 discloses the process for the preparation of 10-hydroxy-9-alkyl analogs of camptothecin.

A need continues to exist for the development of new and better camptothecin and homocamptothecin compounds having still higher antitumor activity and still more improved water-solubility while exhibiting low levels of toxicity.

SUMMARY OF THE INVENTION

Accordingly, it is a primary object of the present invention to provide new camptothecin and homocamptothecin compounds including analogs and derivatives displaying cytotoxic activity and improved water-solubility for ease and efficiency of administration/delivery.

Still another object of the present invention is to provide new camptothecin and homocamptothecin drugs including analogs and derivatives, processes for preparing said analogs and derivatives and formulations containing such analogs and derivatives.

Yet another object of this invention is the provision of new camptothecin and homocamptothecin drugs including derivatives possessing high anti-tumor activity and water solubility and minimal toxicity.

Other objects and advantages of the present invention will become apparent as the description thereof proceeds. In satisfaction of the foregoing objects and advantages, there is provided by this invention camptothecin and homocamptothecin drugs having the structures shown below.

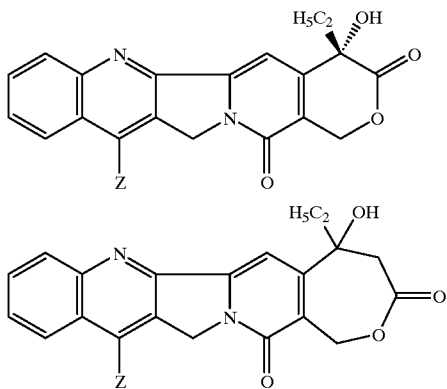

The compounds of the present invention are prepared by substitution of the 7-position of camptothecins or 12-position of homocamptothecins to form water-soluble compounds containing an aminoalkyl moiety. The aminoalkyl moiety may incorporate either an unbranched or branched alkyl chain. The homocamptothecin structure can be readily prepared starting from camptothecin according to a published method (Bigg et al., Biorganic and Medicinal Chemistry Letters (1997) 17 2235–2238) or can be prepared following derivitazation at position 7. Generally, the camptothecins serving as starting materials are suspended in organic solvents or water, stirred and cooled. To the mixture is added the following compounds which give equivalent structure to Z: halo alcohols, amino alcohols, amino aldehydes, halo aldehydes, halo ketones, azido alcohols, azido aldehydes, sulfuric acid, iron sulfate and oxidizing reagents such as peracids and hydrogen peroxide. The mixture is then stirred to complete the reaction. Any precipitate which forms is removed by filtration and the product is isolated after removal of the solvent.

Z in the structure shown above is:

A) $C_{1-20}$ $NR^1R^2$ where
  (1) $R^1$ is hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl and $R^2$ is $C_{1-20}$ $NR^3R^4$ where: (a) $R^3$ and $R^4$ are independently, hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, 3–7 membered heterocyclic ring which may contain a O, S or N group; (b) $R^3$ is hydrogen and $R^4$ is $C_{1-18}$ alkyl, $C_{3-7}$ cycloalkyl, $C_{3-7}$ cycloalkyl-C, alkyl, $C_{2-18}$ alkenyl, hydroxy-$C_{1-18}$ alkyl or $C_{1-18}$ alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy, $C_{1-18}$ alkoxy-$C_{1-18}$ alkyl; (c) $R^3$ and $R^4$ taken together with the nitrogen atom to which they are attached form a saturated 3–7-membered heterocyclic ring which may contain a O, S or $NR^5$ group, where $R^5$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and $-COR^6$ where $R^6$ is hydrogen, $C_{1-6}$ alkyl, perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups, (2) $R^1$ is hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, and $R^2$ can be any one of the following alkylamines or alkyl polyamines or a corresponding salt form:

—$(CH_2)_3NH_2$
—$(CH_2)_4NH_2$
—$(CH_2)_5NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)_3NH((CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH_3)NH(CH_2)_4NH_2$ (3) $R^1$ is hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, and $R^2$ can be either $CO(OCH_2)_nOR^{10}$ or $CH_2(OCH_2)_nOR^{10}$ where n=1–2, 000 and $R^{10}$ is either hydrogen. $C_{1-10}$ alkyl, or aryl.

(4) $NR^1R^2$ is guanidino group; and (5) $R^1$ is hydrogen, $C_{1-8}$ alkyl, $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl, $R^2$ is $C_{1-8}$ alkyl-$SiR^{11}R^{12}R^{13}$ where $R^{11}$, $R^{12}$, and $R^{13}$ are methyl or $R^{11}$, $R^{12}$, and $R^{13}$ are independently $C_{1-10}$ alkyl, $C_{2-8}$ alkenyl, $C_{2-8}$ alkynyl $C_{1-8}$ alkoxy, $C_{1-8}$ aminoalkyl, $C_{1-8}$ hydroxyalkyl, and haloalkyl groups.

B) $C_{2-20}$ $NR^1R^2$ where (a) $R^1$ and $R^2$ taken together with the nitrogen atom to which they are attached form a saturated 3–7-membered heterocyclic ring which may contain a O, S or $NR^3$ group, where $R^3$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and $COR^4$ where $R^4$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

C) $C_{12-20}$ $NR^1R^2$ where (1) $R^1$ and $R^2$ are independently, hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl or (2) $R^1$ is hydrogen and $R^2$ is $C_{1-18}$ alkyl, $C_{3-7}$ cycloalkyl, $C_{3-7}$ cycloalkyl-$C_{1-18}$ alkyl, $C_{2-18}$ alkenyl, hydroxy, $C_{1-18}$ alkyl or $C_{1-18}$ alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy, $C_{1-18}$ alkoxy-$C_{1-18}$ alkyl.

D) $NR^1R^2$ where $R^1$ is hydrogen, $C_{1-8}$ alkyl, $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl, and $R^2$ is one of the following alkylamines or alkylpolyamines or a corresponding salt form:

—$(CH_2)_3NH_2$
—$(CH_2)_4NH_2$
—$(CH_2)_5NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH,(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)_3NH(CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH_3)NH(CH_2)_4NH_2$

E) $C_{1-8}OR$ where
R is $CONR^1 R^2$ and $R^1$ is hydrogen, $C_{1-8}$ alkyl, $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl, and $R^2$ is one of the following alkylamine or alkylpolyamine or corresponding salt form substituents:

—$(CH_2)_3NH_2$
—$(CH_2)_4NH_2$
—$(CH_2),NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_3NH(CH_2)_3NH(CH_2)_4NH_2$
—$(CH_2)_3NH(CH_2)_4NH(CH_2)_3NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NIH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)3NH(CH_2)_3NH(CH_2)_4NH(CH_2)_3NH_2$
—$(CH_2)_3NH(CH_2)_3NIH(CH_2)_4NH(CH_2)_3NH(CH_2)_3NH_2$
—$C(NH)NH(CH_2)_4NH_2$
—$C(NCH_3)NH(CH_2)_4NH_2$

Preferred aryl groups are phenyl and naphthyl. Suitable heterocyclic rings defined by a covalent association between $R^3$ and $R^4$ and the nitrogen atom to which they are attached include the following: aziridine, azetidine, pyrolidine, piperidine, hexamethylenimine, imidazolidine, pyrazolidine, isoxazoline, piperazine, methylpiperazine, homopiperazine, -methyl-homopiperazine and thiazolidine.

The free amine of any of the compounds of the present invention may be converted to an acid addition salt by the addition of a pharmaceutically acceptable acid well known in the art to be suitable for this purpose. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate, stearate, quaternary ammonium, and trifluoroacetate salts. The salts may be purified by crystallization from a suitable solvent such as water or ethanol.

Advantageously, the novel compounds/drugs of the present invention exhibit a number of unique properties and characteristics which when considered in combination clearly establish the superiority of these compounds for use in antitumor therapy and treatment. The novel compounds display good biological activity while also possessing favorable characteristics for active loading into liposomal particle drug delivery systems of the type disclosed and described in U.S. Pat. Nos. 5,316,771, 5,552,156 and 5,736,156 to Burke. In this document it is demonstrated that pre-made liposomes can be efficiently loaded with the novel compounds of this invention using pH gradients.

In addition, the novel compounds/drugs display enhanced water solubility. Accordingly, there is reduced membrane binding which means that the compounds/drugs of the present invention tend to reside in the more aqueous inner compartments of the liposome away from the membrane components. As a result, the compounds/drugs are fully held in an environment where they are protected from physiological pH during delivery to the tumor site. As a consequence, the compounds/drugs remain more stable in their anti-tumor active lactone form and are thus more efficiently and effectively delivered to the site of cancer cells. There the compounds/drugs diffuse out of the liposome and inhibit tumor growth by inhibiting the DNA synthesis and reversibly fragmenting the DNA of the cancer cells.

The claimed compounds/drugs with polyamine substitution include a linking-alkyl chain between the nitrogen substituted group and the pyridine ring which provide a number of advantages.

An increase in the number of nitrogen atoms present in the C-7 substituent in camptothecins and the C-12 substituent in homocamptothecins increases the effective positive charge of the molecule, thereby giving the agent better solubility and allowing the compounds to still interact with important cellular components such as membranes and the topoisomerase I enzyme. In addition, different lengths of alkyl linkage between the nitrogen atoms produce different activities (for example the polyamine analogs BE-3-3-3, BE-3-7-3, BE-4-4-4-4).

The provision of substituents on the pyridine ring with more than 1 nitrogen atom (polyamine like structures) is also important for the following reasons:

a. The stability of the lactone form (and anticancer activity as well) increases in key biological matrices such as human blood.

b. The utility of the polyamine analogs as single agents is enhanced for a variety of tumor types, due to the ability to combine such agents with other therapeutic modalities. Previous studies have shown that the depletion of polyamine like structures produced by DFMO, MGBG, or other inhibitors of polyamine biosynthesis could modify the activity of other DNA-directed chemotherapeutic agents, such as the chloroethylnitrosoureas; cisplatinum, and topoisomerase related agents such as 4'-(9-acrydinyl-amino) methanesulfon-M-anisidide (M-AMSA). Thus, the presence of polyamine-like structures could modulate the activities of other anticancer drugs used in combination with the compounds/drugs of the present invention.

Figure 1:
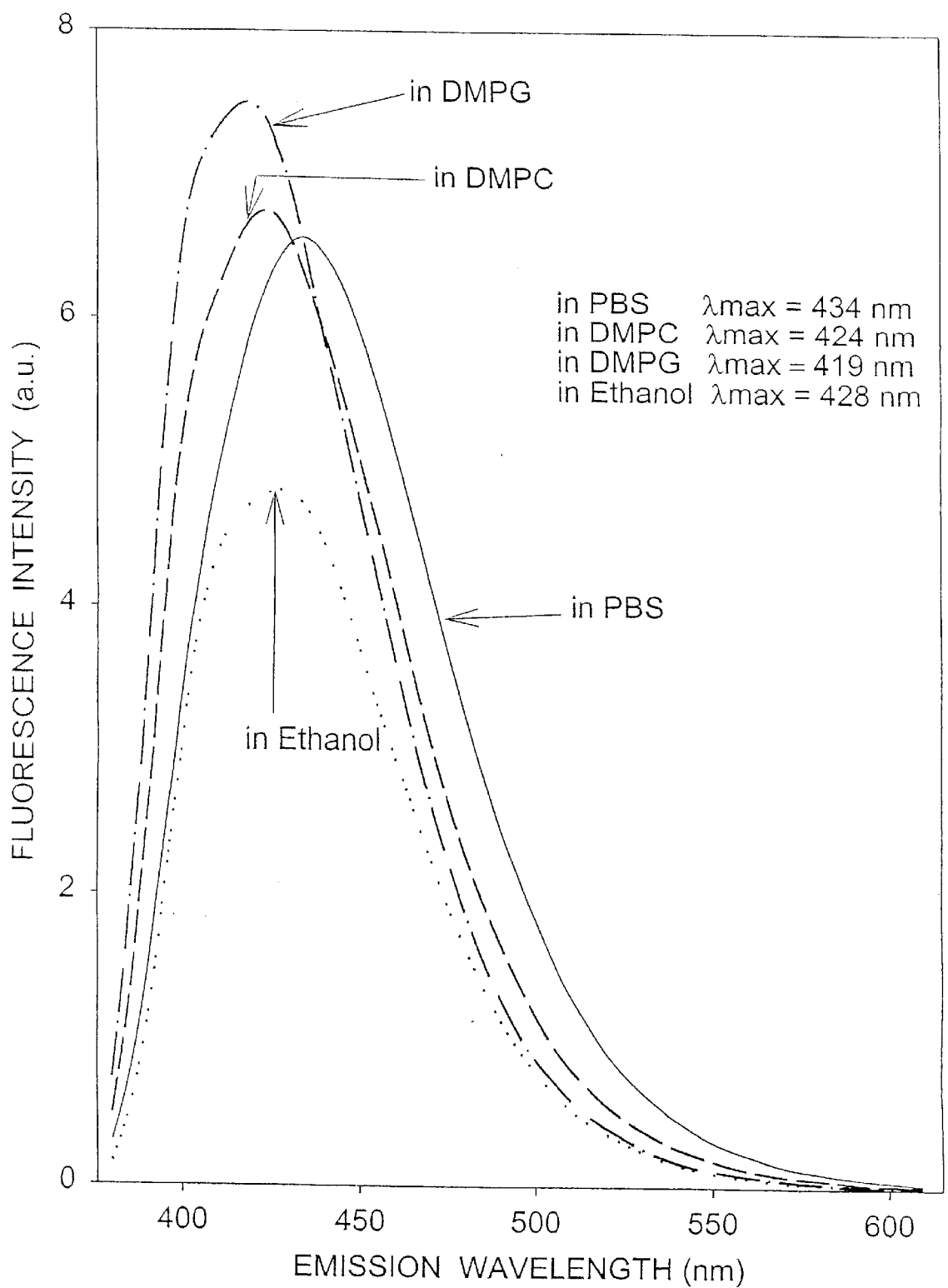
FIG. 1 is the fluorescence emission spectra of 1 μM of 7-(1-Aminoethyl)camptothecin (7AEC) in various solvents and suspensions such as phosphate buffered saline, ethanol, and phosphate buffered saline containing small unilamellar vesicles (SUVs) composed either of dimyristoylphosphatidylcholine (DMPC) or dimyristoylphosphatidlyglycerol (DMPG). Experiments were conducted at 37° C. using exciting light of 370 nm. Note that in the presence of liposomes composed of either DMPC or DMPG the fluorescence emission spectra of 7AEC shifts to shorter wavelength, indicative of drug interaction with the membranes (lipid concentration 0.04M, λex=370 nm, EX resolution 4 nm, EM resolution 4 nm, without EM polarizer, HV=810 V).

However, CT-17 can be actively loaded and retained in liposomal particles (unlike camptothecin and SN-38), thereby allowing advanced liposome-based tumor targeting to be used to deliver very high concentrations of CT-17 selectively to the tumor site.

DETAILED DESCRIPTION OF THE INVENTION

As previously described, the present invention relates to novel camptothecin and homocamptothecin analogs/drugs (hereinafter referred to as "compounds") many of which incorporate polyamine moieties. Unlike the monoamine derivatives such as 7AEC described in the prior art, the presence of polyamine substituents at the 7 position in the camptothecin compounds and the 12 position in the homocamptothecin compounds means that the compounds of the present invention are characterized by the spread of a positive charge over a greater surface area. This advantageously results in compounds of increased water-solubility which also exhibit reduced membrane binding.

Advantageously, compounds of the present invention and particularly those camptothecin analogs/derivatives with a polyamine substituent at the 7 position and those homocamptothecin compounds with a polyamine substituent at the 12 position display reduced membrane binding but are still capable of crossing membranes in response to a pH gradient. Accordingly, the compounds of the present invention may be readily actively loaded into liposomal particles such as the particles described in U.S. Pat. Nos. 5,316,771, 5,552,156 and 5,736,156, the disclosures of which are all fully incorporated herein by reference. Since DNA is highly negatively-charged, the widespread positive charge of the polyamine bearing compounds of the present invention enhances interaction of those compounds with DNA. The resulting compound-DNA interaction functions to further stabilize the compound in its active lactone form as described by Yang et al. in PCT/US 98/20941. Further, the positively-charged polyamine functionalities of the present compounds discourages compound binding with blood proteins such as albumin and this reduced blood protein binding promotes more efficient and effective antitumor activity against cancer cells.

As an additional benefit, the linking alkyl chain provided between the nitrogen substituent and the pyridine ring may be lengthened or shortened to control the distance over which the positive charge character is spread. Thus, the compounds of the present invention may be tailored to provide desired water solubility, membrane interaction, DNA interaction and plasma protein interaction characteristics to meet the particular needs and application of the compound in treating various types of cancer cells (eg. colon, lung, breast, malignant melanoma).

The compounds of the present invention are generally prepared by substitution of the 7-position of camptothecins such as the parent drug camptothecin and the 12 position of homocamptothecins with water-soluble aminoalkyl moieties resulting in a more water-soluble drug. The aminoalkyl moieties may incorporate both unbranched and branch alkyl chains. To achieve this end the camptothecin/homocamptothecin is suspended in organic solvents such as DMSO, DMF and CHCl$_3$ or water where it is stirred and cooled to approximately −10−25° C. Halo alcohols, amino alcohols, amino aldehydes, halo aldehydes, halo ketones, azido alcohols, azido aldehydes, sulfuric acid, iron sulfate and oxidizing reagents such as peracids and hydrogen peroxide are then added to the mixture. The mixture is stirred to complete the reaction over a time frame of approximately 4–24 hours at a temperature of approximately −10−25° C. Any precipitate that forms is removed by filtration and the product is isolated after removal of the solvent. Solvent removal may be completed by any appropriate means known in art including rotary evaporator.

Compounds of the present invention include those having the following structures:

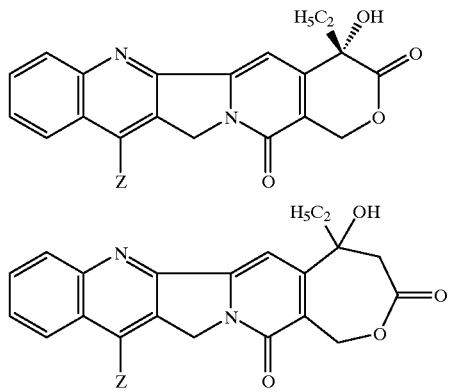

Where Z is:
A) $C_{1-20} NR^1R^2$ where
(1) $R^1$ is hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl and $R^2$ is $C_{1-20} NR^3R^4$ where (a) $R^3$ and $R^4$ are independently, hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, 3–7-membered heterocyclic ring which may contain a O, S or N group; (b) $R^3$ is hydrogen and $R^4$ is $C_{1-18}$ alkyl, $C_{3-7}$ cycloalkyl, $C_{3-7}$ cycloalkyl-$C_{1-18}$ alkyl, $C_{2-8}$ alkenyl, hydroxy-$C_{1-18}$ alkyl or $C_{1-18}$ alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy, $C_{1-18}$ alkoxy-$C_{1-18}$ alkyl; (c) $R^3$ and $R^4$ taken together with the nitrogen atom to which they are attached form a saturated 3–7-membered heterocyclic ring which may contain a O, S or $NR^5$ group, where $R^5$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and —$COR^6$ where $R^6$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;
(2) $R^1$ is hydrogen, $C_{3-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, and $R^2$ is one of the following alkylamines or alkylpolyamines or a corresponding salt form:

—(CH$_2$)$_3$NH$_2$
—(CH$_2$)$_4$NH$_2$
—(CH$_2$)$_5$NH$_2$
—(CH$_2$)$_3$NH(CH$_2$)$_3$NH$_2$
—(CH$_2$)$_3$NH(CH$_2$)$_4$NH$_2$
—(CH$_2$)$_3$NH(CH$_2$)$_5$NH$_2$
—(CH$_2$)$_4$NH(CH$_2$)$_4$NH$_2$
—(CH$_2$)$_3$NH(CH$_2$)$_3$NH(CH$_2$)$_3$NH$_2$
—(CH$_2$)$_3$NH(CH$_2$)$_3$NH(CH$_2$)$_4$NH$_2$
—(CH$_2$)$_3$NH(CH$_2$)$_3$NH(CH$_2$)$_7$NH$_2$

—$(CH_2)_3NH(CH_2)4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_33NH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)_3NH(CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH_3)NH(CH_2)_4NH_2$ (3) $R^1$ is hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, and the following polyamines; $R^2$ is $CO(OCH_2)_nOR^{10}$, and $CH_2$—$(OCH_2)_nOR^{10}$ where n=1–2,000 and $R^{10}$ is either hydrogen, $C_{1-10}$ alkyl, aryl.

(4) $NR^1R^2$ is guanidino group; and (5) $R^1$ is hydrogen, $C_{1-8}$ alkyl, $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl, $R^2$ is $C_{1-8}$ alkyl-$SiR^{11}R^{12}R^{13}$ where $R^{11}$, $R^{12}$, $R^{13}$ are methyl or $R^{11}$, $R^{12}$, and $R^{13}$ are independently $C_{1-10}$ alkyl, $C_{2-8}$ alkenyl, $C_{2-8}$ alkynyl $C_{1-8}$ alkoxy $C_{1-8}$ aminoalkyl, $C_{1-8}$ hydroxyalkyl, haloalkyl groups.

B) $C_{2-20}$ $NR^1R^2$ where (a) $R^1$ and $R^2$ taken together with the nitrogen atom to which they are attached form a saturated 3–7-membered heterocyclic ring which may contain a O, S or $NR^3$ group, where $R^3$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and —$COR^4$ where $R^4$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

C) $C_{12-20}$ $NR^1R^2$ where (1) $R^1$ and $R^2$ are independently, hydrogen, $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl or (2) $R^1$ is hydrogen and $R^2$ is $C_{1-18}$ alkyl, $C_{3-7}$ cycloalkyl, $C_{3-7}$ cycloalkyl-$C_{1-18}$ alkyl, $C_{2-18}$ alkenyl, hydroxy, $C_{1-18}$ alkyl or $C_{1-18}$ alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy, $C_{1-18}$ alkoxy-$C_{1-18}$ alkyl.

D) $NR^1R^2$, where $R^1$ is hydrogen, $C_{1-18}$ alkyl, $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl, and $R^2$ is one of the following alkylamines or alkylpolyamines or a corresponding salt form:

—$(CH_2)_3NH_2$
—$(CH_2)_4NH_2$
—$(CH_2)_5NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)_3NH(CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH_3)NH(CH_2)_4NH_2$

E) $C_{1-8}OR$ where
R is $CONE R^2$; $R^1$ is hydrogen, $C_{1-8}$ alkyl $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$ alkyl and $R^2$ is one of the following alkylamines or alkylpolyamine or corresponding salt form substituents:

—$(CH_2)_3NH_2$
—$(CH_2)_4NH_2$
—$(CH_2)_5NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NH(CH_2)_3NH(CH_2)_3NH(CH_2)_3NH_2$
—$(CH_2)_3NH(CH_2)_3NH(CH_2)_3NH(CH_2)_3NH(CH_2)_4NH_2$
—$(CH_2)_3NH(CH_2)_3NH(CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH_3)NH(CH_2)_4NH_2$

The free amine of any of the compounds of the present invention may be converted to an acid addition salt by the addition of a pharmaceutically acceptable acid. Suitable acids known to be useful for such a purpose include both inorganic and organic acids. Suitable addition salts include, but are not limited to hydrochloride, sulfate, phosphate, diphosphate, hydrobromide, nitrate, acetate, malate, maleate, fumarate, tartrate, succinate, citrate, lactate, methanesulfonate, p-toluenesulfonate, palmoate, salicylate and stearate salts. The salts may be purified by crystallization from a suitable solvent such as ethanol or water.

Camptothecin and homocamptothecin have an asymmetric carbon atom at the α-position and β-position, respectively, and therefore exist in two enantiomeric forms, i.e. the (R) and (S) configurations. Other camptothecins and homocamptothecins also exist in two enantiomeric forms. This invention includes both enantiomeric forms of camptothecins and homocamptothecins and all combinations of these forms, including racemic mixtures designated as (RS).

The 7-modified camptothecin and 12-modified homocamptothecins compounds of the invention are administered in a dose which is effective at inhibiting the enzyme topoisomerase I. These effective amounts are generally from about 1–80 mg/kg of body weight per week, preferably about 2–40 mg/kg per week. The compounds of this invention may be administered in much higher doses than the corresponding parent compounds, because the compounds of the invention are anticipated to have substantially less toxicity than the parent compounds. This is likely because modification at the C-7 position in camptothecins and C-12 position in homocamptothecins promotes higher levels of lactone in the presence of albumin. Liposomal encapsulation also enhances the blood lactone levels of the polyamine compounds of the present invention. The polyamine compounds display high retention in liposomal carriers dispersed in blood because of the reduced membrane interactions of the compounds, allowing the agents to be better retained in the internal aqueous compartments of the particles. While not being bound by any particular scientific theory, it is believed that the lower toxicity of the present compounds is due to the water solubility and reduced membrane and albumin binding of the modified compounds. In any event, the α-hydroxyl of camptothecin analogs and β-hydroxy of homocamptothecin analogs is thought to be required in underivatized form for camptothecin, homocamptothecin and analogs/derivatives to be optimally potent antileukemia and anti-tumor agents. This property of the present compounds is surprisingly advantageous in optimizing the macromolecular interactions and drug delivery characteristics of the compounds for optimal use in therapy In addition, it is well-known that the lactone ring of camptothecin, homocamptothecin and their analogs/derivatives opens to a physiologically inactive open form at physiological pH, 7.2, (J. Fassberg and V. J. Stella, J. Pharm. Sci. (1992) 81: 676–684; T. G. Burke, A. K. Mishra, M. C. Wani, and M. E. Wall, Biochem., 32(20), 5352 (1993)). The compounds of the present invention may be administered as a pharmaceutical composition containing the compounds and a pharmaceutically acceptable carrier or diluent. The compounds can be administered as their ring open salt forms, since relactonization to their active forms can occur in the body (especially at sites of reduced pH). The active material can also be mixed with other active materials which do not impair the desired action and/or supplement the desired action. The active materials according to the present invention can be administered by any route, for example, orally, nasally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water:for injection, suspensions of liposomal particles whereby the particles contain stable, active drug within the core of the particle in a pH controlled and protected environment or associated to the outside of the particle or any of the bilayers of the particle, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablet. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such a colloidal silicon dioxide; and a sweetening agent such as sucrose or saccharin or flavoring agent such as peppermint, methyl salicylate, or orange flavoring may be added. When the dosage unit is in the form of a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition the active compounds, sucrose as a sweetening agent and certain preservatives, dyes and coloring and flavors. Materials used in preparing these various compositions should be pharmaceutically or veterinarally pure and non-toxic in the amount used.

The following synthesis and examples are presented to further illustrate the present invention, but is not to be considered as limited thereto. In the examples, NMR spectra were obtained using a Varian VXR 300 MHz Instrument and mass spectra were obtained using an Ion Spec Mass Spectrometer.

EXAMPLE 1

7-Chloromethylcamptothecin (Chem. Pharm. Bull. 1991, 39, 2574):

To a suspension of camptothecin (3.00 g, 8.6 mmol) in a mixture of chloroacetaldehyde (18 ml) and $H_2O$ (75 ml), 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h and then diluted with $H_2O$, extracted with chloroform (3×200 ml), and the organic layer was washed with brine and dried over $MgSO_4$. Evaporation of the solvent gave a brown oil which was purified using column chromatography (eluent: chloroform: methanol 98:2). The product was isolated as a yellow solid. 7-Chloromethylcamptothecin (3.0 g, 88% yield) was yielded in the form of pale yellow prisms. Melting point (MP) 261–262° C., IR (K Br) v: 1770, 1665, 1605 $cm^{-1}$. $^1H$-NMR (DMSO-$d_6$) δ: 0.89 (3H, t, J=7 Hz), 1.88 (2H, q, J=7 Hz), 4.27 (2H, s, 7-$CH_2Cl$), 5.40 (2H, s, $C_5$—$H_2$), 5.80 (2H, s, $C_{17}$—$H_2$), 6.50 (1H, s, 20-OH), 7.33 (1H, s, $C_{14}$—H), 7.60–8.21 (4H, m, arom).Ms m/z: 396 ($M^+$). Anal. Calcd for $C_{21}H_{17}ClN_2O_4$ (396.83): C, 63.56: H, 4.32: N, 7.06. Found: C, 63.32; H, 4.60; N, 7.27.

EXAMPLE 2
7-(1-Chloropropyl)camptothecin:

To a suspension of camptothecin (3.00 g, 8.6 mmol) in a mixture of 4-chlorobutanal (3 g, 30 mmol) and $H_2O$ (75 ml). 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), and the organic layer was washed with brine and dried over $MgSO_4$. Evaporation of the solvent gave a brown oil which was purified using column chromatography (eluent: chloroform: methanol 98:2). The product was isolated as a yellow solid. The yield of 7-(1-chloropropyl)camptothecin was 3.1 g (85% yield, yellow solid). MP 215–216° C. IR (K Br) v: 1760, 1660, 1605 $cm^{-1}$. $^1$H-NMR (DMSO-$d_6$) δ: 0.89 (3H, t, J=7 Hz), 1.88 (2H, q, J=7 Hz), 2.22–2.29 (m, 2H, CH2), 3.37 (m, 2H, CH2), 4.41 (2H, m, 7-$CH_2Cl$), 5.40 (2H, s, $C_5$—$H_2$), 5.80 (2H, S, $C_{17}$—$H_2$), 6.50 (1H, s, 20-OH), 7.33 (1H, s, $C_{14}$—H), 7.60–8.21 (4H, m, arom).Ms m/z: 424 ($M^+$). Anal. Calcd for $C_{23}H_{21}ClN_2O_4$ (424.88): C, 65.02: H, 4.98: N, 6.59. Found: C, 65.33; H, 4.60; N, 6.27.

EXAMPLE 3
7-(1-Chloropentyl)camptothecin:

To a suspension of camptothecin (3.00 g, 8.6 mmol) in a mixture of 6-chlorohexanal (6.9 g, 50 mmol) and $H_2O$ (75 ml), 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h and then diluted with $H_2O$, and extracted with chloroform (3×200 ml). The organic layer was washed with brine and dried over $MgSO_4$. Evaporation of the solvent gave a brown oil which was purified using column chromatography (eluent: chloroform: methanol 98:2). The product was isolated as a yellow solid. The yield of 7-(1-chloropenthyl)camptothecin was (3.98 g, 88% yield, yellow solid). MP 254–255° C. IR (K Br) v: 1770, 1665, 1605 $cm^{-1}$. $^1$H-NMR (DMSO-$d_6$) δ: 0.89 (3H, t, J=7 Hz), 1.15–2.31 (m, 10H, 5CH2), 3.23 (m, 2H, CH2), 4.41 (m, 2H, 7-$CH_2Cl$), 5.40 (2H, S, $C_5$—$H_2$), 5.80 (2H, S, $C_{17}$—$H_2$), 6.50 (1H, s, 20-OH), 7.33 (1H, S, $C_{14}$—H), 7.60–8.21 (4H, m, arom).Ms m/z: 452 ($M^+$). Anal. Calcd for $C_{25}H_{25}ClN_2O_4$ (452.94): C, 66.03: H, 5.56: N, 6.18. Found: C, 66.33; H, 5.62; N, 6.27.

EXAMPLE 4
7-(1-Azidoethyl)camptothecin:

To a suspension of camptothecin (3.00 g, 8.6 mmol) in a mixture of 3-azidopropanal (4.9 g, 50 mmol) and $H_2O$ (75 ml), 75% $H_2SO_4$ (75 ml) was added dropwise. and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), and the organic layer was washed with brine and dried over $MgSO_4$. Evaporation of the solvent gave a brown oil which was purified using column chromatography (eluent: chloroform: methanol 98:2). The product was isolated as yellow solid. The yield of 7-(1-azidoethyl)camptothecin was 2.94 g (82% yield, yellow solid). MP 193–194° C. IR (K Br) v: 2020, 1770, 1665, 1605 $cm^{-1}$. $^1$H NMR (CDCl$_3$) δ 8.28 (1H, d, J 7.3 Hz), 8.o7 (1H, d, J 7.4 Hz), 7.84 (1H, m), 7.75–7.67 (2H, m), 5.77 (1 h, d, J 16.4 Hz), 5.37–5.28 (3H, m), 3.84 (2H, t, J 6.6 Hz), 3.43 (2H, t, J 7.0 Hz), 1.93–1.84 (2H, m), 1.05 (3H, t, 7.4 Hz).Ms m/z: 452 ($M^+$). Anal. Calcd for $C_{22}H_{19}N_5O_4$ (417.42): C, 63.30: H, 4.59: N, 16.78. Found: C, 63.53; H, 4.62; N, 16.07. High resolution mass spectrometry (HRMS) M+: calcd. for $C_{22}H_{19}N_5O_4$: 417.1437; found: 417.1438.

EXAMPLE 5
7-(1-Azidopropyl)camptothecin:

To a suspension of camptothecin (3.00 g, 8.6 mmol) in a mixture of 4-azidobutanal (5.51 g, 50 mmol) and $H_2O$ (75 ml), 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h and then diluted with $H_2O$, extracted with chloroform (3×200 ml), and the organic layer was washed with brine and dried over $MgSO_4$. Evaporation of the solvent gave a brown oil which was purified using column chromatography (eluent: chloroform: methanol 98:2). The product was isolated as a brown solid. The yield of 7-(1-azidopropyl)camptothecin was: 3.15 g, 85% yield, yellow solid. MP 209–210° C. IR (K Br) v: 2020, 1770, 1660, 1605 $cm^{-1}$. $^1$H NMR (CDCl$_3$) δ 8.22 (1H, d, J 8.5 Hz), 8.08 (1H, d, J 8.4 Hz), 7.79 (1H, m), 7.68–7.63 (2H, m), 5.74 (1H, d, J 16.4 Hz), 5.33–5.26 (3H, m), 3.46 (2H, 6.2 Hz), 3.26 (1H, 7.4 Hz), 2.08–1.84 (4H, m), 1.02 (3H, t, J 6.5 Hz).Ms m/z: 431 ($M^+$). Anal. Calcd for $C_{23}H_{21}N_5O_4$ (431.35): C, 64.03: H, 4.91: N, 16.23. Found: C, 64.33; H, 4.62; N, 16.31. HRMS of M+calcd. For $C_{23}H_{21}N_5O_4$: 431.1593. Found: 431.1595.

EXAMPLE 6
7-(1-Azidobutyl)camptothecin:

To a suspension of camptothecin (3.00 g, 8.6 mmol) in a mixture of 5-azidopentanal (6.3 g, 50 mmol) and $H_2O$ (75 ml), 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h and then diluted with $H_2O$, extracted with chloroform (3×200 ml), organic layer was washed with brine and dried over $MgSO_4$. Evaporation of the solvent gave a brown oil which was purified using column chromatography (eluent: chloroform: methanol 98:2). The product was isolated as a brown solid. Yield of 7-(1-azidopropyl) camptothecin: 3.28 g, 82% yield, yellow solid. MP 227–228° C. IR (K Br) v: 2020, 1765, 1660, 1610 $cm^{-1}$. $^1$H NMR (CDCl$_3$) δ 8.24 (1H, d, J 8.5 Hz), 8.09 (1H, d, J 8.7 Hz), 7.77 (1H, m), 7.72–7.68 (1H, m), 5.76 (1H, d, J 8.2 Hz), 5.35–5.27 (3H, m), 3.63 (2H, d, J 6.0Hz), 3.26 (1H, 7.7 Hz), 1.93–1.78 (6H, m), 1.04 (3H, t, J 7.3 Hz).Ms m/z: 445 ($M^+$). Anal. Calcd for $C_{24}H_{23}N_5O_4$ (445.48): C, 64.71: H, 5.2: N, 15.72. Found: C, 64.43; H, 5.38; N, 15.41. HRMS of M+for $C_{24}H_{23}N_5O_4$: calculated: 445.1750; Found: 445.1752.

EXAMPLE 7
7-(1-Azidopentyl)camptothecin:

To a suspension of camptothecin (3.00 g, 8.6 mmol) in a mixture of 6-azidohexanal (7.05 g, 50 mmol) and $H_2O$ (75 ml). 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), and the organic layer was washed with brine and dried over $MgSO_4$. Evaporation of the solvent gave a brown oil which was purified using column chromatography (eluent: chloroform: methanol 98:2). The product was isolated as a brown solid. Yield of 7-(1- azidodentyl)camptothecin (3.43 g, 87% yield)yellow solid. MP 234–235° C. IR (K Br) v: 2020, 1760, 1650, 1610 cm$^{-1}$. $^1$H NMR (CDCl$_3$) δ 8.23 (1H, d, J=7.7 Hz), 8.06 (1H, d, J 7.7 Hz), 7.78 (1H, m), 7.74–7.64 (2H, m), 5.74 (1H, d, J 16.4 Hz), 5.36–5.23 (3H, m), 3.30 (2H, t, J 6.2Hz), 3.18 (2H, t, 7.7Hz), 2.00–1.50 (8H, m), 1.03 (3H, t, J 7.3 Hz).Ms m/z: 459 (M$^+$). Anal. Calcd for (459.5): C, 65.35: H, 5.48: N, 15.24. Found: C, 65.43; H, 5.33; N, 15.31. HRMS of M+value for $C_{25}H_{25}N_5O_4$, calculated (459.1906), found (459.1910).

EXAMPLE 8
7-(1-aminoethyl)camptothecin (HCl salt):

A mixture of 7-(1-azidoethyl)camptothecin (1 mmol, 417 mg), and Ph$_3$P (1.2 mmol) in THF-H$_2$O (99/1, 5 mL) was stirred overnight at 20° C. (Mitsunobu et al. Synthesis, 1981,) and then to this mixture 2 N HCl (1 mL) and water (10 mL) was added. The water layer was separated and washed with CHCl$_3$ (3×10 mL) and ether (3×10 mL) and dried over magnesium sulfate and filtrated. Evaporation of the solvent gave a crude which was recrystallized to afford the hydrochloric salt of the amine (yield 419 mg, 98%). The sample exhibited a MP>275° C. and decomposed. The sample was recrystallized from H$_2$O—MeOH. $^1$H NMR (D$_2$O) δ 7.72–7.63 (2H, m), 7.54 (1H, m), 7.35 (1H, m), 5.35 (1H, d, J 16.5 Hz), 5.21 (1H, cl), 4.77 (2H, m), 3.34 (2H, m), 3.21 (2H, m), 1.81) 2H, m), 0.84 (13H, t, J 7 Hz).$C_{22}H_{22}ClN_3O_4$(427.89).

EXAMPLE 9
7-(1-aminopropyl)camptothecin (HCl salt):

A mixture of 7-(1-azidopropyl)camptothecin (1 mmol, 431 mg), and Ph$_3$P (1.2 mmol) in THF-H$_2$O (99/1, 5 mL) was stirred overnight at 20° C. (Mitsunobu et al. Synthesis, 1981) then to this mixture 2 N HCl (1 mL) and water (10 mL) was added. The water layer was separated and washed by CHCl$_3$ (3×10 mL) and ether (3×10 mL) and dried over magnesium sulfate and filtrated. Evaporation of the solvent gave a crude which was recrystallized to afford the hydrochloric salt of the amine (yield 420 mg, 95%). M.p.>280° C., decomposed. Recrystallized from H$_2$O—MeOH. $^1$H NMR (D$_2$O) δ 7.55 (1H, m), 7.47 (1H, s), 7.39 (1H, m), 7.27 (1H, m), 5.32 (1H, d, J 16.1 Hz), 5.19 (1H, d), 4.4819 (2H, s), 3.04 (2H, t, J 7.5 Hz), 2.92 (2H, d), 1.84 (4H, m), 0.86 (3H, t, J 7.1 Hz). $C_{23}H_{24}ClN_3O_4$ (441.91).

EXAMPLE 10
7-(1-aminobutyl)camptothecin (HCl salt):

A mixture of 7-(1-azidobutyl)camptothecin (1 mmol, 445 mg), and Ph$_3$P (1.2 mmol) in THF-H$_2$O (99/1, 5 mL) was stirred overnight at 20° C. (Mitsunobu et al. Synthesis, 1981) and then to this mixture 2 N HCl (1 mL) and water (10 mL) was added. The water layer was separated and washed by CHCl$_3$ (3×10 mL) and ether (3×10 mL) and dried over magnesium sulfate and filtrated. Evaporation of the solvent gave a crude which was recrystallized to afford the hydrochloric salt of the amine (yield 428 mg, 94%). M.p.>278–9° C., decomposed. Recrystallized from H$_2$O—MeOH. $^1$H NMR (D$_2$O) δ 7.58 (1H, d, J 8.7 Hz), 7.46–7.35 (3H, m), 7.17 (1H, m), 5.17 (1H, d, J 16.5 Hz), 4.55 (1H, d), 4.43 (2H, s), 2.92–2.80 (4H, m), 1.82–1.47 (6H, m), 0.83 (1H, t, J 7.3 Hz).$C_{24}H_{26}ClN_3O_4$ (455.94).

EXAMPLE 11
7-(1-aminopentyl)camptothecin (HCl salt):

A mixture of 7-(1-azidopenthyl)camptothecin (1 mmol, 459 mg), and Ph$_3$P (1.2 mmol) in THF-H$_2$O (99/1, 5 mL) was stirred overnight at 20° C. (Mitsunobu et al., Synthesis, 1981) and then to this mixture 2 N HCl (1 mL) and water (10 mL) was added. The water layer was separated and washed by CHCl$_3$ (3×10 mL) and ether (3×10 mL) and dried over magnesium sulfate and filtrated. Evaporation of the solvent gave a crude which was recrystallized to afford the hydrochloric salt of the amine (yield 432 mg, 92%). M.p.>255–6° C., decomposed. Recrystallized from H$_2$O—MeOH. $^1$H NMR (DMSO-d$_6$) δ 8.24 (1H, d, J 7.0 Hz), 7.80 (1H, m), 7.73 (1H, m), 5.42 (2H, s), 5.26 (2H, s), 3,14 (2H, m), 2.74 (2H, m), 1.85 (2H, m), 1.66–1.51 (6H, m), 8.87 (3H, t, J 6.8 Hz). $C_{25}H_{28}ClN_3O_4$ (469.97).

EXAMPLE 12
7-(1-Guanidinoethyl)camptothecin (H$_2$SO$_4$ salt):

To a solution of 7-(1-aminoethyl)camptothecin (1.9 g, 5 mmol) in 10 ml of water was added S-methylisothiourea hemisulfate (0.7 g, 2.5 mmol) at room temperature. The mixture was heated at 50° C. for 5 hr under nitrogen. The gases developed during the reaction were passed through two flasks, each containing an ethanolic solution of KOH for trapping the CH$_3$SH by-product. The mixture was then concentrated and 50 ml of acetone was added. The precipitate was filtered and recrystallized from water to give 2.60 g (98%) of guanidine sulfate. Colorless solid, M.p. 286–287° C. (decomposed). IR (KBr): 2400–2600, 1760, 1660 cm$^{-1}$. $^1$H-NMR (DMSO-d$_6$) δ: 0.89 (3H, t, J=7 Hz), 1.88 (2H, q, J=7 Hz), 2.55–2.95 (4H, m, CH2 and CH$_2$-guanidine.), 5.40 (2H, S, C$_5$—H$_2$), 5.80 (2H, S, C$_{17}$—H$_2$), 6.50 (1H, s, 20-O), 7.33 (1H, S, C$_{14}$—H), 7.60–8.21 (4H, m, arom).Ms m/z: 531 (M$^+$). Anal. Calcd for $C_{23}H_{25}N_5O_8S$ (531.55): C, 51.97: H, 4.74: N, 13.18. Found: C, 51.88; H, 4.60; N, 13.32.

EXAMPLE 13
7-(1 -Guanidinopropyl)camptothecin (H$_2$SO$_4$ salt):

To a solution of 7-(1-aminopropyl)camptothecin (2.0 g, 5 mmol) in 10 ml of water was added S-methylisothiourea hemisulfate (0.7 g, 2.5 mmol) at room temperature. The mixture was heated at 50° C. for 5 hr under nitrogen. The gases developed during the reaction were passed through two flasks, each containing an ethanolic solution of KOH for trapping the CH3SH by-product. The mixture was then concentrated and 50 ml of acetone was added. The precipitate was filtered and recrystallized from water to give 2.59 g (95%) of guanidine sulfate. Colorless solid, MP 265–267° C.(dec.). IR (KBr): 2400–2600, 1770, 1650 cm$^{-1}$. $^1$H NMR (D$_2$O) δ 7.55 (1H, m), 7.47 (1H, s), 7.39 (1H, m), 7.27 (1H, m), 5.32 (1H, d, J 16.1 Hz), 5.19 (1H, d), 3.04 (2H, t, J 7.5 Hz), 2.92 (2H, d), 1.84 (4H, m), 0.86 (3H, t, J 7.1 Hz). $C_{24}H_{27}N_5O_8S$ (545.57). Ms m/z: 545 (M$^+$). Anal. Calcd for $C_{24}H_{27}N_5O_8S$ (545.57): C, 52.84: H, 4.99: N, 12.84. Found: C, 52.88; H, 4.63; N, 13.12.

EXAMPLE 14
7-(1-Guanidinobutyl)camptothecin (H$_2$SO$_4$ salt):

To a solution of 7-(1-aminobutyl)camptothecin (2.10 g, 5 mmol) in 10 ml of water was added S-methylisothiourea hemisulfate (0.7 g, 2.5 mmol) at room temperature. The mixture was heated at 50° C. for 5 hr under nitrogen. The gases developed during the reaction were passed through two flasks, each containing an ethanolic solution of KOH for trapping the CH$_3$SH by-product. The mixture was then concentrated and 50 ml of acetone was added. The precipitate was filtered and recrystallized from water to give 2.60 g (93%) of guanidine sulfate. Colorless solid, MP 292–293° C.(dec.). IR (KBr): 2400–2620, 1775, 1650 cm$^{-1}$. $^1$H NMR (D$_2$O) δ 7.58 (1H, d, J 8.7 Hz), 7.46–7.35 (3H, m), 7.17 (1H, m), 5.17 (1H, d, J 16.5 Hz), 4.55 (1H, d), 2.98 (2H, m), 2.92–2.80 (4H, m), 1.82–1.47 (6H, m), 0.83 (1H, t, J 7.3 Hz). $C_{25}H_{29}N_5O_8S$ (559.6). Ms m/z: 559 (M$^+$). Anal. Calcd for $C_{25}H_{29}N_5O_8S$ (559.6): C, 53.66: H, 5.22: N, 12.51. Found: C, 53.56; H, 5.41; N, 12.34.

EXAMPLE 15
7-(1-Guanidinopentyl)camptothecin ($H_2SO_4$ salt):

To a solution of 7-(1-aminopentyl)camptothecin (2.16 g, 5 mmol) in 10 ml of water was added S-methylisothiourea hemisulfate (0.7 g, 2.5 mmol) at room temperature. The mixture was heated at 50° C. for 5 hr under nitrogen. The gases developed during the reaction were passed through two flasks, each containing an ethanolic solution of KOH for trapping the $CH_3SH$ by-product. The mixture was then concentrated and 50 ml of acetone was added. The precipitate was filtered and recrystallized from water to give 2.72 g (95%) of guanidine sulfate. Colorless solid, MP 289–291° C.(dec.). IR (KBr): 2400–2620, 1775, 1650 cm$^{-1}$. $^1$H NMR (DMSO-d$_6$) δ 8.24 (1H, d, J 7.0 Hz), 7.80 (1H, m), 7.73 (1H, m), 5.42 (2H, s), 5.26 (2H, s), 3,11 (2H, m), 2.96 (2H, m), 1.82 (2H, m), 1.66–1.51 (6H, m), 8.87 (3H, t, J 6.8 Hz). $C_{26}H_{31}N_5O_8S$ (573.63). Ms m/z: 573 (M$^+$). Anal. Calcd for $C_{26}H_{31}N_5O_8S$ (573.63): C, 54.44: H, 5.45: N, 12.21. Found: C, 54.68; H, 5.31; N, 12.38.

EXAMPLE 16
7-[N-(2-(4-morpholino)ethyl)aminomethyl] -(20S) camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 2 ml of 4-ethylaminomorpholine in 20 ml of dry toluene. The reaction mixture was allowed to stir for 2 h after which the reaction mixture was concentrated to a thick residue under high vacuum followed by purification by column chromatography using silica gel (CHCl$_3$/MeOH 95:5). The evaporation of solvent gave 88 mg (36%) of 7-N-(2-(4-morpholino)ethyl)methylamino-(20S) camptothecin as a yellow solid. MP 196–198° C. (d). IR (K Br) ν: 1770, 1665, 1605 cm$^{-1}$. $^1$HNMR: (CDCl$_3$): δ 1.04 (t, J=7.2H$_2$, 3H, CH$_3$), 1.88–2.82 (m, 3CH$_2$, 6H), 3.35–3.88 (m, 2CH$_2$, 4H), 5.22–5.72 (m, 3H), 7.66–7.71 (m, 2H, AR—H), 7–78 (m, 1H), 8.16 (d, J=8.1 H$_7$, 1H), 8.23 (d, J=7.8H$_7$, 1H). HRMS calcd. for $C_{27}H_{30}N_4O_5$ 491.229 (MH+), found 491.228 (MH+).

EXAMPLE 17
7-[N-(2-(1-Pyrrolidino) ethyl)aminomethyl]-(20S)-camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 3 ml of 1-ethylaminopyrrolidine in 20 ml of dry toluene. The reaction mixture was allowed to stir for 2 h after which the reaction mixture was concentrated to a thick residue under high vacuum followed by purification by column chromatography using silica gel (CHCl3/MeOH, 90:10). The evaporation of solvent gave 88 mg (37%) of 7-[N(2-(1-Pyrrolidino) ethyl)methylamino]-(20S)-camptothecin as a yellow solid. MP 181–183° C. (d). IR (K Br) ν: 1770, 1665, 1610 cm$^{-1}$. $^1$H-NMR(CDCl$_3$) (ppm):1.04 (3H, t), 1.2 (2H, q), 1.8–2.2 (4H, t), 2.4–2.6 (4H, t), 2.8–3.1 (6H, m), 5.2 (2H, m), 5.7 (2H, d, 16.4 Hz), 6.7 (1H, d, J=7.4 Hz), 7.6 (1H, d, J=7.3 Hz), 7.7 (1H, d, J=7.4 Hz), 8.02–8.1 (2H, m).High Resolution Mass Spectrum: Calcd. MH$^+$: 475.2345 ; Found: 475.234.

EXAMPLE 18
7-[N-(4-methyl-1-piperazino)aminomethyl]-(20S)-camptothecin (CT-17):

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 3 ml of 4-methylpiperazine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 90:10). The evaporation of solvent gave 100 mg (42%) of 7-[N-(4-methyl-1-piperazino) methylamino]-(20S)-camptothecin as a yellow solid. MP 167–169° C. (d). IR (K Br) ν: 1770, 1660, 1610 cm$^{-1}$. $^1$H-NMR(CDCl$_3$) (ppm): 0.9 (3H, t), 1.2 (2H, c, 2.3–2.6 (8H, m), 2.7 (2H, s), 2.9 (3H, s) 5.3–5.5 (4H, m), 6.6 (1H, d, J=16.3 Hz), 7.7 (1H, d, J=8.2 Hz), 7.9 (1H, d, J=8.4 Hz), 8.5 (2H, m). High Resolution Mass Spectrum for $C_{26}H_{29}N_5O_4$: Calcd. MH$^+$: 476.230; Found: 476.231.

EXAMPLE 19
7-[N-(2-(1-Piperidino) ethyl)aminomethyl]-(20S)-camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 3 ml of 1-ethylaminopiperidine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 90:10). The evaporation of solvent gave 93 mg (38%) of 7-[N-(2-(1-Piperidino) ethyl)aminomrethyl]-(20S)-camptothecin as a yellow solid. MP 171–1173° C. (d). IR (K Br) ν: 1760, 1650, 1610 cm$^{-1}$. $^1$H-NMR(CDCl$_3$) (ppm): 0.9 (3H, t), 1.1 (2H, q), 1.8–2.1 (6H, m), 2.3–2.6 (4H, t), 2.7–3.1 (6H, m), 5.2 (2H, m), 5.6 (2H, d, J=8.2 Hz), 6.7 (1H, d, J=8.4 Hz), 7.6 (1H, d, J=8.3 Hz), 7.7 (1H, d, J=8.3 Hz), 8.02–8.1 (2H, m). $C_{28}H_{32}N_4O_4$ (488.59) High Resolution Mass Spectrum for $C_{28}H_{32}N_4O_4$: Calcd. MH$^+$: 489.250; Found: 489.249.

EXAMPLE 20
7-[N-(4-morpholino) aminomethyl]-(20S)-camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 2 ml of 4-aminomorpholine in 20 ml of dry toluene. The reaction mixture was allowed to stir for 2 h after which the reaction mixture was concentrated to a thick residue under high vacuum followed by purification by column chromatography using silica gel (CHCl$_3$/MeOH, 95:5). The evaporation of solvent gave 88 mg (36%) of 7-[N-(4-morpholino) methylamino]-(20S)- camptothecin as a yellow solid. MP 171–173° C. (d). IR (K Br) ν: 1770, 1665, 1610 cm$^{-1}$. $^1$HNMR: (CDCl$_3$): δ 1.04 (t, J=7.2H$_2$, 3H, CH$_3$), 1.83–2.82 (m, 2CH$_2$, 4H), 3.35–3.78 (m, 2CH$_2$, 4H), 5.22–5.71 (m, 3H), 7.66–7.71 (m, 2H, AR—H), 7–78 (m, 1H), 8.16 (d, J=8.1 H$_7$, 1H), 8.23 (d, J=7.8H$_7$, 1H). HRMS calcd. for $C_{25}H_{27}N_4O_5$ 464.2059 (MH+), found 464.2061 (MH+).

EXAMPLE 21
7-[N-(4-hydroxymethyl-1-piperazino)aminomethyl]-(20S)-camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 3 ml of 4-hydroxymethylmethylpiperazine in 20 ml of dry toluene. The reaction mixture was allowed to stir for 5 h after which the reaction mixture was concentrated to a thick residue under high vacuum followed by purification by column chromatography using silica gel ($CHCl_3$/MeOH, 98:2 then 80:20). The evaporation of solvent gave 110 mg (43%) of 7-[N-(4-hydroxymethyl-1-piperazino)aminomethyl]-(20S)-camptothecin as a yellow solid. MP 197–199° C. (d). IR (K Br) v: 3200, 1770, 1660, 1610 $cm^{-1}$. $^1$H-NMR($CDCl_3$) (ppm): 0.9 (3H, t), 1.2 (2H, q), 2.3–2.6 (8H, m), 2.7 (2H, s), 4.7 (2H, s) 5.3–5.5 (4H, m), 6.6 (1H, d, J=16.3 Hz), 7.7 (1H, d, J=8.2 Hz), 7.9 (1H, d, J=8.4 Hz), 8.5 (2H, m). $C_{26}H_{29}N_5O_5$ (491.55). High Resolution Mass Spectrum for $C_{26}H_{29}N_5O_5$: Calcd. $MH^+$: 492.2246; Found: 492.2244.

EXAMPLE 22
7-[N-(2-(S)-methoxymethyl pyrrolidino)aminomethyl]-(20S)-camptothecin:

To a dry 100 ml round bottom flask fitted with a magnetic stir bar was added 198 mg (0.5 mmol) of 7-chloromethylcamptothecin and 20 ml dry dimethylsulfoxide. The mixture was allowed to stir until all the solid was dissolved. To the remaining solution was added a solution of 3 ml of (S)-1-amino-2-methoxymethylpyrrolidine in 20 ml of dry toluene. The reaction mixture was allowed to stir for 5 h after which the reaction mixture was concentrated to a thick residue under high vacuum followed by purification by column chromatography using silica get ($CHCl_3$/MeOH, 98:2 then 85:15). The evaporation of solvent gave 96 mg (39%) of 7-[N-(2-(S)-methoxymethyl pyrrolidino)methylamino]-(20S)-camptothecin as a yellow solid. MP 158–159° C. (d). IR (K Br) v: 1770, 1660, 1610 $cm^{-1}$. $^1$H-NMR($CDCl_3$) (ppm): 0.9 (3H, t), 1.2 (2H, q), 1.52–1.63 (m, 4H, 2$CH_2$ pyrrolidine ring), 2.3–2.8 (m, 2$CH_2$, 4H), 3.58 (s, 3H, $OCH_3$), 3.46–4.21 (m, CH, $CH_2$, 3H pyrrohldine ring), 5.3–5.5 (4H, m), 6.6 (1H, d, J=16.3 Hz), 7.7 (1H, d, J=8.2 Hz), 7.9 (1H, d, J=8.4 Hz), 8.5 (2H, m). $C_{27}H_{30}N_4O_5$ (490.56). High Resolution Mass Spectrum for $C_{26}H_{21}N_5O_5$: Calcd. $MH^+$: 491.2294; Found: 491.2291.

EXAMPLE 23
7-[3-N-(2-(4-morpholino)ethyl)aminopropyl]-(20S) camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 2 ml of 4-ethylaminomorpholine in 20 ml of dry toluene. The reaction mixture was allowed to stir for 2 h after which the reaction mixture was concentrated to a thick residue under high vacuum followed by purification by column chromatography using silica gel ($CHCl_3$/MeOH, 95:5). The evaporation of solvent gave 99 mg (38%) of 7-[3-N-(2-(4-morpholino)ethyl) aminopropyl]-(20S) camptothecin as a yellow solid. MP 177–178° C. (d). IR (K Br) v: 1770, 1665, 1605 $cm^{-1}$. $^1$HNMR: ($CDCl_{13}$): δ 1.04 (t, J=7.2$H_2$, 3H, $CH_3$), 1.68–2.82 (m, 5$CH_2$, 1OH), 3.33–3.86 (m, 2$CH_2$, 4H), 5.23–5.71 (m, 3H), 7.68–7.73 (m, 2H, AR—H), 7.78 (m, 1H), 8.16 (d, J=8.1 $H_7$, 1H), 8.21 (d, J=7.8$H_7$, 1H). $C_{29}H_{34}N_4O_5$ (518.61). HRMS calcd. for $C_{29}H_{34}N_4O_5$ 519.2607 (MH+), found 519.2602 (MH+).

EXAMPLE 24
7-[3-N-(2-(1-Pyrrolidtino) ethyl)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 3 ml of 1-ethylaminopyrrolidine in 20 ml of dry toluene. The reaction mixture was allowed to stir for 4 h after which the reaction mixture was concentrated to a thick residue under high vacuum followed by purification by column chromatography using silica gel ($CHCl_3$/MeOH, 98:2 then 90:10). The evaporation of solvent gave 1.08 g (43%) of 7-[3-N-(2-(1-Pyrrolidino) ethyl)aminopropyl]-(20S)-camptothecin as a yellow solid. MP 181–183° C. (d). IR (K Br) v: 1770, 1665, 1610 $cm^{-1}$. $^1$H-NMR($CDCl_3$) (ppm): 1.04 (3H, t), 1.21 (2H, q), 1.78–2.71 (m, 8H, 3$CH_2$), 2.41–2.63 (4H, t), 2.81–3.12 (6H, m), 5.2 (2H, m), 5.7 (2H, d, 16.4 Hz), 6.7 (1H, d, J=7.4 Hz), 7.6 (1H, d, J=7.3 Hz), 7.7 (1H, d, J=7.4 Hz), 8.02–8.1 (2H, m). $C_{29}H_{34}N_4O_4$ (502.61). High Resolution Mass Spectrum: Calcd. $MH^+$: 503.2658; Found: 503.2656.

EXAMPLE 25
7-[3-N-(4-methyl-1-piperazino)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 4 ml of 4-methylpiperazine in 20 ml of dry toluene. The reaction mixture was allowed to stir for 6 h after which the reaction mixture was concentrated to a thick residue under high vacuum followed by purification by column chromatography using silica gel ($CHCl_3$/MeOH, 98:2 then 90:10). The evaporation of solvent gave 110 mg (44%) of 7-[3-N-(4-methyl-1-piperazino)aminopropyl]-(20S)-camptothecin as a yellow solid. MP 166–168° C. (d). IR (K Br) v: 1760, 1650, 1610 $cm^{-1}$. $^1$H-NMR($CDCl_3$) (ppm): 0.91 (3H, t), 1.22 (2H, q), 1.89–2.61 (12H, m), 2.69 (2H, s), 2.92 (3H, s) 5.32–5.45 (4H, m), 6.63 (1H, d, J=16.3 Hz), 7.67 (1H, d, J=8.2 Hz), 7.92 (1H, d, J=8.4 Hz), 8.48 (2H, m). $C_{28}H_{33}N_5O_4$ (503.6). High Resolution Mass Spectrum for $C_{21}H_{33}N_5O_4$: Calcd. $MH^+$: 504.2610; Found: 504.2612.

EXAMPLE 26
7-[3-N-(2-(1-Piperidino) ethyl)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 4 ml of 1-ethylaminopiperidine in 20 ml of dry toluene. The reaction mixture was allowed to stir for 6 h after which the reaction mixture was concentrated to a thick residue under high vacuum followed by purification by column chromatography using silica gel ($CHCl_3$/MeOH, 98:2 then 90:10). The evaporation of solvent gave 95 mg (38%) of 7-[3-N-(2-(1-Piperidino) ethyl)aminopropyl]-(20S)-camptothecin as a yellow solid. MP 179–181° C. (d). IR (K Br) v: 1770, 1650, 1610 $cm^{-1}$. $^1$H-NMR($CDCl_3$) (ppm): 0.91 (3H, t), 1.12 (2H, q), 1.68–2.18 (1 OH, m), 2.3–2.6 (4H, t), 2.71–3.09 (6H, m), 5.18 (2H, m), 5.6 1 (2H, d, J=8.2 Hz), 6.72 (1H, d, J=8.4 Hz), 7.56 (1H, d, J=8.3 Hz), 7.71 (1H, d, J=8.3 Hz), 8.02–8.13 (2H, m). $C_{29}H_{34}N_4O_4$ (502.60). High Resolution Mass Spectrum for $C_{29}H_{34}N_4O_4$: Calcd. MH$^+$: 503.2658 ; Found: 503.2657.

EXAMPLE 27
7-[3-N-(4-morpholino)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 4 ml of 4-aminomorpholine in 20 ml of dry toluene. The reaction mixture was allowed to stir for 2 h after which the reaction mixture was concentrated to a thick residue under high vacuum followed by purification by column chromatography using silica gel ($CHCl_3$/MeOH, 95:5). The evaporation of solvent gave 100 mg (42%) of 7-[3-N-(4-morpholino) aminopropyl]-(20S)-camptothecin as a yellow solid. MP 166–168° C. (d). IR (K Br) v: 1770, 1665, 1610 cm$^{-1}$. $^1$HNMR: (CDCl$_3$): δ 1.02 (t, J=7.2H$_2$, 3H, CH$_3$), 1.73–2.81 (m, 4CH$_2$, 8H), 3.33–3.78 (m, 2CH$_2$, 4H), 5.24–5.69 (m, 3H), 7.66–7.71 (m, 2H, AR—H), 7.78 (m, 1H), 8.18 (d, J=8.1 H$_7$, 1H), 8.21 (d, J=7.8H$_7$, 1H). $C_{27}H_{31}N_4O_5$ (491.57) .HRMS calcd. for $C_{27}H_{31}N_4O_5$ 491.229 (M+), found 491.228 (M+).

EXAMPLE 28
7-[3-N-(4-hydroxymethyl-1-piperazino)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 4 ml of 4-hydroxymethylmethylpiperazine in 20 ml of dry toluene. The reaction mixture was allowed to stir for 6 h after which the reaction mixture was concentrated to a thick residue under high vacuum followed by purification by column chromatography using silica gel ($CHCl_3$/MeOH, 98:2 then 80:20). The evaporation of solvent gave 110 mg (41%) of 7-[3-N-(4-hydroxymethyl-1-piperazino)aminopropyl]-(20S)-camptothecin as a yellow solid. MP 181–183° C. (d). IR (K Br) v: 3250, 1770, 1660, 1610 cm$^{-1}$. $^1$H-NMR (CDCl$_3$) (ppm): 0.91 (3H, t), 1.23 (2H, q), 1.75–2.61 (10H, m), 2.71 (2H, s), 4.72 (2H, s) 5.31–5.52 (4H, m), 6.63 (1H, d, J=16.3 Hz), 7.71 (1H, d, J=8.2 Hz), 7.89 (1H, d, J=8.4 Hz), 8.52 (2H, m). $C_{28}H_{33}N_5O_5$ (519.60). High Resolution Mass Spectrum for $C_{28}H_{33}N_5O_5$: Calcd. M$^+$: 519.2481; Found: 519.2478.

EXAMPLE 29
7-[3-N-(2-(S)-methoxymethyl pyrrolidino)aminopropyl]-(20S)-camptothecin:

To a dry 100 ml round bottom flask fitted with a magnetic stir bar was added 212 mg (0.5 mmol) of 7-(1-chloropropyl) camptothecin and 20 ml dry dimethylsulfoxide. The mixture was allowed to stir until all the solid was dissolved. To the remaining solution was added a solution of 3 ml of (S)-1-amino-2-methoxymethylpyrrolidine in 20 ml of dry toluene. The reaction mixture was allowed to stir for 5 h after which the reaction mixture was concentrated to a thick residue under high vacuum followed by purification by column chromatography using silica gel ($CHCl_3$/MeOH, 98:2 then 85:15). The evaporation of solvent gave 110 mg (43%) of 7-[3-N-(2-(S)-methoxymethyl pyrrolidino)aminopropyl]-(20S)-camptothecin as a yellow solid. MP 152–154° C. (decomposed). IR (K Br) v: 1770, 1660, 1610 cm$^{-1}$. $^1$H-NMR(CDCl$_3$) (ppm): 0.92 (3H, t), 1.22 (2H, q), 1.52–1.63 (m, 8H, 2CH2 pyrrolidine ring and 2CH$_2$), 2.32–2.78 (m, 2CH$_2$, 4H),3.58 (s, 3H, OCH$_3$),3.46–4.21 (m, CH, CH$_2$, 3H pyrrolidine ring), 5.31–5.52 (4H, m) 6.63 (1H, d, =16.3 Hz), 7.71 (1H, d, J=8.2 Hz), 7.89 (1H, d, J=8.4 Hz), 8.53 (2H, m). $C_{29}H_{34}N_4O_5$ (518.61). High Resolution Mass Spectrum for $C_{29}H_{34}N_4O_5$: Calcd. M$^+$: 519.2529 : 519.2528.

EXAMPLE 30
7-[5-N-(2-(4-morpholino)ethyl)aminopenthyl]-(20S) camptothecin:

To a dry 100 ml round bottom flask fitted with a magnetic stir bar was added 266 mg (0.5 mmol) of 7-(1-chloropentyl) camptothecin and 20 ml dry dimethylsulfoxide. The mixture was allowed to stir until all the solid was dissolved. To the remaining solution was added a solution of 3 ml of 4-ethylaminomorpholine in 20 ml of dry toluene. The reaction mixture was allowed to stir for 4h after which the reaction mixture was concentrated to a thick residue under high vacuum followed by purification by column chromatography using silica gel ($CHCl_3$/MeOH, 95:5). The evaporation of solvent gave 110 mg (39%) of 7-[5-N-(2-(4-morpholino)ethyl)aminopentyl ]-(20S) camptothecin as a yellow solid. MP 167–168° C. (d). IR (K Br) v: 1770, 1660, 1610 cm$^{-1}$. $^1$HNMR: (CDCl$_3$): δ1.04 (t, J=7.2H$_2$, 3H, CH$_3$), 1.11–2.82 (m, 7CH$_2$, 14H), 3.31–3.86 (m, 2CH$_2$, 4H), 5.23–5.68 (m, 3H), 7.68–7.72 (m, 2H, AR-H), 7.78(m, 1H), 8.15(d, J=8.1 H$_7$, 1H), 8.18 (d, J=7.8H$_7$, 1H). $C_{31}H_{38}N_4O_5$ (546.67). HRMS calcd. for $C_{31}H_{38}N_4O_5$ 546.2842 (M +), found 546.2840 (M +).

EXAMPLE 31
7-5-N-(4-methyl-1-piperazino)aminopentyl]-(20S)-camptothecin:

To a dry 100 ml round bottom flask fitted with a magnetic stir bar was added 226 mg (0.5 mmol) of 7-(1-chloropentyl) camptothecin and 20 ml dry dimethylsulfoxide. The mixture was allowed to stir until all the solid was dissolved. To the remaining solution was added a solution of 4 ml of 4-methylpiperazine in 20 ml of dry toluene. The reaction mixture was allowed to stir for 5 h after which the reaction mixture was concentrated to a thick residue under high vacuum followed by purification by column chromatography using silica gel ($CHCl_3$/MeOH, 98:2 then 90:10). The evaporation of solvent gave 98 mg (37%) of 7-[5-N-(4-methyl-1-piperazino)aminopentyl]-(20S)-camptothecin as a yellow solid. MP 183–185° C. (d). IR (K Br) v: 1760, 1650, 1610 cm$^{-1}$. $^1$H-NMR(CDCl$_3$) (ppm): 0.91 (3H, t), 1.12–1.66 (6H, m), 1.89–2.60 (12H, m), 2.67 (2H, s), 2.92 (3H, s) 5.32–5.41 (4H, m), 6.62 (1H, d, J=16.3 Hz), 7.66 (1H, d, J=8.2 Hz), 7.91 (1H, d, J=8.4 Hz), 8.43 (2H, m). $C_{30}H_{37}N_5O_4$ (531.66). High Resolution Mass Spectrum for $C_{30}H_{37}N_5O_4$: Calcd. MH$^+$: 532.2845 ; Found: 532.2843.

EXAMPLE 32
7-N-(2-N-(2-Aminoethyl)-aminoethyl)aminomethyl-(20S)-camptothecin (HCl Salt) (using nonprotected diethylenetriamine):

A 15 ml round bottom flask equipped with a magnetic stir bar was charged with 198 mg (0.5 mmol) of 7-chloromethylcamptothecin and 5 ml of anhydrous N,N-dimethylformamide under dry nitrogen. The dark brown solution was stirred and cooled to 78° C., and the mixture was then treated with diethylenetriamine (3 ml, 30 mmol) the cooling bath was removed and the mixture was allowed to stir for 3 h. The solvent was removed by rotary evaporator at high vacuum and the resulting residue was dissolved in CHCl$_3$ and washed with 2N HCl and the water layer was separated and removed from the flask. The aqueous fraction was then washed again with CHCl$_3$ and dried under vacuum. The product was purified by HPLC using a reversed-phase chromatography column. Yield: 85 mg 34%

¹HNMR(DMSOd6): δ0.98 (t, J=14H₇, 3H, CH₃), 1,82–2.21 (m, 2H, CH₂), 2.71–3.82 (m, 1OH, 5CH₂), 5.52 (m, 4H), 7.22–7.63 (m, 4H), 7.81 (d, J=7.2H₇, 1H), 8.32 (d, J=7.4, 1H). HRMS calcd for C₂₅H₂₉N₅O₄ HCl 500.1975 found 500.227 (M+H).

EXAMPLE 33
7-N-(2-N-(2-Aminoethyl)-aminoethyl)aminomethyl -(20S)-camptothecin (HCl Salt) (using protected diethylenetriamine):

A 15 ml round bottom flask equipped with a magnetic stir bar was charged with 198 mg (0.5 mmol) of 7-chloromethylcamptothecin and 5 ml of anhydrous N,N-dimethylformamide under dry nitrogen. The dark brown solution was stirred and cooled to 78° C., and the mixture was then treated with di-Boc protected diethylenetriamine (2 ml) prepared according to a published procedure (Blagbrough et al. J. Chem. Soc. Chem. Commun. 1998, 1403; Tetrahedron Lett. 1998, 39, 443; Synthesis, 1984, 1032; Greene, Protective groups in organic synthesis, Wiley, 1991). The cooling bath was removed and the mixture was allowed to stir for 3 h. The solvent was removed by rotary evaporator at high vacuum and the resulting residue was dissolved in CHCl₃ and to this solution was added 10 ml 3N HCl solution. The sample was stirred at room temperature and the water layer was separated and removed. The aqueous phase was washed again with CHCl₃ and dried under vacuum. The product was purified by HPLC using a reversed-phase chromatography column. Yield: 107 mg, 43%.

EXAMPLE 34
7-3-[N-(2-N-(2-Aminoethyl)-aminoethyl)aminopropyl -(20S)-camptothecin (HCl Salt): A 15 ml round bottom flask equipped with a magnetic stir bar was charged with 212 mg (0.5 mmol) of 7-(1-chloropropyl)camptothecin and 5 ml of anhydrous N,N-dimethylformamide under dry nitrogen. The dark brown solution was stirred and cooled to 78° C., and the mixture was then treated with di-Boc protected diethylenetriamine (prepared according to published procedures: Blagbrough et al. J. Chem. Soc. Chem. Commun. 1998, 1403; Tetrahedron Lett. 1998, 39, 443; Synthesis, 1984, 1032, Greene, Protective groups in organic synthesis, Wiley, 1991). The volume added was 2 ml. The cooling bath was removed, and the mixture was allowed to stir for 4 h. The solvent was removed by rotary evaporator at high vacuum and the resulting residue was dissolved in CHCl₃ (50 ml) and to this solution was added 10 ml 3N HCl solution. The solution was stirred at room temperature for 2 h and the water layer was separated and removed. The water layer was washed with CHCl₃ and dried under vacuum. The product was purified by HPLC using a reversed-phase chromatography column. Yield: 113 mg, 43%. ¹HNMR(DMSOd6): δ 0.98 (t, J=14H₇, 3H, CH₃), 1,82–2.51 (m, 6H, 3CH₂), 2.67–3.81 (m, 1OH, 5CH₂), 5.53 (m, 4H), 7.22–7.61 (m, 4H), 7.81 (d, J=7.2H₇, 1H), 8.23 (d, J=7.4, 1H). HRMS calcd for C₂₇H₃₃N₅O₄ (3 HCl) 600.1911 (M+H), found 600.188 (M+H).

EXAMPLE 35
7-(2,2,2,2-Pentaminomethyl-(20S)-camptothecin polytrifluoroacetate salt:

A 15 ml round bottom flask equipped with a magnetic stir bar was charged with 106 mg (0.25 mmol) of 7-(1-chloropropyl)camptothecin and 5 ml of anhydrous N,N-dimethylformamide under dry nitrogen. The dark brown solution was stirred and cooled to 78° C., and the mixture was then treated with 1 gram of tetra-Boc protected 2,2,2, 2-pentamine (prepared according to the procedure of Blagbrough et al., J. Chem. Soc. Chem. Commun. 1998, 1403; Tetrahedron Lett. 1998, 39, 443, Synthesis, 1984, 1032, Greene, Protective groups in organic synthesis, Wiley, 1991). The cooling bath was removed, and the mixture was allowed to stir for 4 h. The solvent was removed by rotary evaporator at high vacuum and the resulting residue was dissolved in CHCl₃ (50 ml) and to this solution was added 10 ml 3N HCl solution and stirred at room temperature for 2 hours. The aqueous layer was removed and washed again with CHCl₃ and dried under vacuum. The product was purified by HPLC using a reversed-phase chromatography column. The yield was 61 mg. ¹HNMR(DMSOd6): δ 0.98 (m, 3H, CH₃), 1.82–3.52 (m, 20H, CH₂), 5.53 (m, 4H), 7.22–7.61 (m, 4H), 7.81 (m, 1H), 8.23 (m, 1H).

EXAMPLE 36
7-M-PEG(5000)aminomethyl (20S) camptothecin:

A 15 ml round bottom flask equipped with a magnetic stir bar was charged with 40 mg (0.1 mmol) of 7-chloromethylcamptothecin and 5 ml of anhydrous N,N-dimethylformamide and 5 ml of DMSO under dry nitrogen. The dark brown solution was stirred and cooled to 78° C., and the mixture was then treated with 4 grams of M-PEG-Amine (5000) (Shearwater Polymer Inc.). The cooling bath was removed and the reaction mixture was allowed to stir for 15 hours after which the reaction mixture was concentrated to a thick residue under high vacuum followed by purification by column chromatography using silica gel (CHCl₃/MeOH 98:2). The evaporation of solvent gave 125 mg of 7-M-PEG(5000)aminomethyl (20S) camptothecin as a yellow solid. MP 113–115° C. IR (K Br) v: 1770, 1665, 1610 cm⁻¹. ¹H-NMR (DMSO-d₆) δ: 0.89 (3H, t, J=7 Hz), 1.88 (2H, q, J=7 Hz), 2.7 (broad s, CH2 of PEG), 5.40 (2H, S, C₅—H₂), 5.80 (2H, S, C₁₇—H₂), 6.50 (1H, s, 20-OH), 7.33 (1H, S, C₁₄—H), 7.60–8.21 (4H, m, arom).

EXAMPLE 37
7-[5-(M-PEG(5000)amino)pentyl (20S) camptothecin:

A 15 ml round bottom flask equipped with a magnetic stir bar was charged with 45 mg (0.1 mmol) of 7-(5-chloropentyl)camptothecin and 5 ml of anhydrous N,N-dimethylformamide and 5 ml of DMSO under dry nitrogen. The dark brown solution was stirred and cooled to 78° C., and the mixture was then treated with 4 grams of M-PEG-Amine (5000) (Shearwater Polymer Inc.). The cooling bath was removed, and the reaction mixture was allowed to stir for 15 hours after which the reaction mixture was concentrated to a thick residue under high vacuum followed by purification by column chromatography using silica gel (CHCl₃/MeOH, 98:2). The evaporation of solvent gave 110 mg of 7-[5-(M-PEG(5000)amino)pentyl (20S) camptothecin as a yellow solid. MP 117–120° C. IR (K Br) v: 1770,1665, 1610 cm⁻¹. ¹H-NMR (DMSO-d₆) δ: 0.89 (3H, t, J=7 Hz), 1.11–1.88 (m, 4CH2, 8h), 2.71 (broad s, CH2 of PEG), 5.43 (2H, s, C₅—H₂), 5.80 (2H, S, C₁₇—H₂), 6.52 (1H, s, 20-OH), 7.33 (1H, s, C₁₄—H), 7.60–8.21 (4H, m, arom).

EXAMPLES 38–74
Homocamptothecin analogs of 7-modified camptothecins are readily prepared from the corresponding a-hydroxy-5-lactone compound (such as those described in Examples 1 through 37) using published methods as shown in Route A on page 95 (Bigg et al., Biorganic and Medicinal Chemistry Letters (1997) 17 2235–2238; Lavergne et al., J. Med. Chem. (1998) 41, 5410–5419). The novel camptothecins described in this document that contain β-hydroxy-δ-lactone E-rings can be treated as follows to prepare the corresponding E-ring expanded β-hydroxy-δ-lactone homocamptothecin analogs. Sodium borohydride reduction of the α-hydroxy-δ-lactone camptothecin analog provides the corresponding 1,2-diols which upon oxidative cleavage induced by periodic acid renders the formlyoxy-mappicine ketone derivatives. A Reformatsky reaction with tert-butyl bromoacetate yield the corresponding β-hydroxy ester, which on reacting with trifluoroacetic acid afford the corresponding homocamptothecin analog. Adjustments in the synthetic methods may be made to suit the compatibility needs of the starting materials.

EXAMPLE 75

12-Chloromethyl-5-ethyl-1,4,5,13-tetrahydro-5-hydroxy-3H,15-H-oxepino[3',4':6,7]indolizino[1,2-b]quinoline-3,15-dione as shown below.

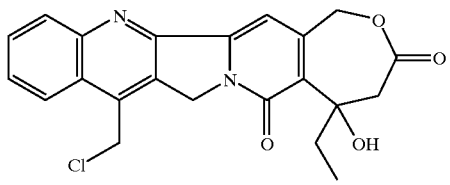

An alternate means of preparing the 12-substituted homocamptothecin analogs of interest involves first preparing homocamptothecin and then substituting at the 12-position. For this synthetic method, homocamptothecin or 5-Ethyl-1,4,5,13-tetrahydro-5-hydroxy-3H,15-H-oxepino[3',4':6,7]indolizino[1,2-b]quinoline-3-15-dione (shown below)

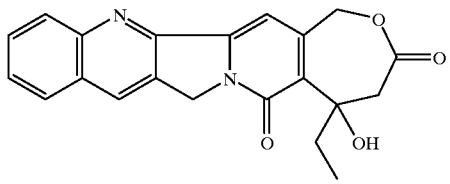

is prepared according to the procedure of Bigg et al. (Bioorg. Med. Chem. Lett. 1997, 17, 2235–2238) by the reduction of camptothecin with sodium borohydride. This furnishes the hydroxylactol which converts to formyloxy-mappicin ketone using periodic acid. The reaction of this ketone with zinc and t-butyl bromoacetate followed treatment with trifluoroacetate affords homocamptothecin. To then derivitize homocamptothecin at the 12-position, a suspension of homocamptothecin (3.12 g, 8.6 mmol) in a mixture of chloroacetaldehyde (18 ml) and $H_2O$ (75 ml) is prepared. 75% $H_2SO_4$ (75 ml) is added dropwise, and then $FeSO_4 7H_2O$ (2.40 g, 8.6 mmol) was added. To the ice-cold mixture, 30% $H_2O_2$ (15 ml, 6.6 mmol) is added dropwise for 2 h with stirring. The mixture is stirred at room temperature for 14 h and then diluted with $H_2O$, extracted with chloroform (3×200 ml), and the organic layer washed with brine and dried over $MgSO_4$. Evaporation of the solvent renders a brown oil which upon purification using column chromatography (eluent: chloroform: methanol 98:2) yields the yellow solid product.

EXAMPLE 76

12-[N-(4-methyl-1-piperazino) aminomethyl]-5-ethyl-1,4,5,13-tetrahydro-5-hydroxy-3H,15-H-oxepino[3',4':6,7]indolizino[1,2-b]quinoline-3,15-dione:

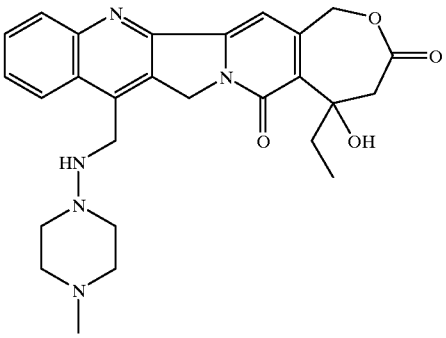

To a dry 100 ml round bottom flask fitted with a magnetic stir bar is added 206 mg (0.5 mmol) of 12-chloromethylhomocamptothecin and 20 ml dry dimethylsulfoxide. The mixture is stirred until all the solid dissolves. To this sample a solution of 3 ml of 4-methylpiperazine in 20 ml of dry toluene is added. The reaction mixture is stirred for 5 h after which the reaction mixture is concentrated to a thick residue under high vacuum followed by purification by column chromatography using silica gel ($CHCl_3$/MeOH, 98:2 then 90:10). The evaporation of solvent renders the product which is a yellow solid.

EXAMPLE 77

Comparison of the Membrane Interactions of the Novel Polyamine Camptothecin Analog 7-[N-(4-methyl-1-piperazino)aminomethyl]-(20S)-camptothecin (CT-17) with 7-(1-Aminoethyl)camptothecin (7AEC).

Chemicals. Camptothecin (CPT) was provided by the National Cancer Institute. SN-38 was obtained from Yakult Honsha. All drugs were in the 20(S) configuration and were of high purity (>98%) as determined by HPLC assays with fluorescence detection. L-α-Dimyristoylphosphatidylcholine (DMPC) and L-α-dimyristoylphosphatidylglycerol (DMPG) were obtained from Avanti Polar Lipids, Alabaster, Ala., and were used without further purification. All other agents were reagent grade and were used without further purification. High purity water provided by a Milli-Q UV PLUS purification system (Bedford, Mass.) was utilized in all experiments.

Drug Stock Solution Preparation. Stock solutions of the drugs were prepared in dimethylsulfoxide (A.C.S. spectrophotometric grade, Aldrich, Milwaukee, Wis.) at a concentration of $2 \times 10^{-3}$ M and stored in dark at 4° C.

Vesicle Preparation. Small unilamellar vesicle (SUV) suspensions were prepared the day of an experiment by the method of Burke et al. (T. G. Burke, A. K. Mishra, M. C. Wani, and M. E. Wall, Lipid Bilayer Partitioning and Stability of Camptothecin Drugs, Biochem., 32(20), 5352 (1993)). Briefly, stock lipid suspensions containing 200 mg/mL lipid in phosphate buffered saline (PBS, pH 7.4) were prepared by Vortex mixing for 5–10 min above the TM of the lipid. The lipid dispersions were then sonicated using a bath-type sonicator (Laboratory Supplies Co., Hicksville, N.Y.) for 3–4 h until they became optically clear. A decrease in pH from 7.4 to 6.8 was observed for the SUV preparations of DMPG; therefore, the pH of these SUV suspensions was adjusted to 7.4 using small quantities of 2.5 M NaOH in PBS, followed by additional sonication. Each type of vesicle suspension was annealed for 30 min at 37° C. and then used in an experiment.

Fluorescence Instrumentation. Steady-state fluorescence measurements were obtained on a SLM Model 9850 spectrofluorometer with a thermostated cuvette compartment. This instrument was interfaced with an IBM PS/2 model 55 SX computer. Excitation and emission spectra were recorded with an excitation resolution of 8 nm and an emission resolution of 4 nm. In all cases spectra were corrected for background fluorescence and scatter from unlabeled lipids or from solvents by subtraction of the spectrum of a blank. Steady-state fluorescence intensity measurements were made in the absence of polarizers. Steady-state anisotropy (a) measurements were determined with the instrument in the "T-format" for simultaneous measurement of two polarized intensities. The alignment of polarizers was checked routinely using a dilute suspension of 0.25 $\mu$m polystyrene microspheres (Polysciences, Inc, Warrington, P.A.) in water and anisotropy values of >0.99 were obtained. Alternatively, polarizer orientation was checked using a dilute solution of glycogen in water. The anisotropy was calculated from $a=(I_{VV}-GI_{VH})/(I_{VV}+2GI_{VH})$, where $G=I_{HV}/I_{HH}$ and the subscripts refer to vertical and horizontal orientations of the excitation and emission polarizers, respectively.

Anisotropy measurements for camptothecins were conducted using exciting light in the range of 370 nm to 400 nm and long pass filters on each emission channel in order to isolate the drug's fluorescence signal from background scatter and/or residual fluorescence. All emission filters were obtained from Oriel Corp (Stamford, Conn.). The combination of exciting light and emission filters allowed us to adequately separate fluorescence from background signal. The contribution of background fluorescence, together with scattered light, was typically less than 1% of the total intensity. Since the lactone rings of camptothecin and related congeners undergo hydrolysis in aqueous medium with half-lives of approximately 20 min., all measurements were completed within the shortest possible time (ca. 0.5 to 1 min) after mixing the drug stock solution with thermally pre-equilibrated solutions such that, in the case of experiments with lactone, the experiments were free of hydrolysis product (or in the case of experiments with carboxylate, the studies were free of lactone).

Determination of Equilibrium Binding Constants. As described previously (T. G. Burke, A. K. Mishra, M. C. Wani, and M. E. Wall, Lipid Bilayer Partitioning and Stability of Camptothecin Drugs, Biochem., 32(20) 5352 (1993), the method of fluorescence anisotropy titration was employed in order to determine the concentrations of free and bound species of drug in liposome suspensions containing a total drug concentration of $1\times10^{-6}$ M and varying lipid concentrations. All experiments were conducted in glass tubes. The overall association constants are defined as $K=[A_B]/[A_F][L]$ where $[A_B]$ represents the concentration of bound drug, $[A_F]$ represents the concentration of free drug, and [L] represents the total lipid concentration of the sample. Double-reciprocal plots of the binding isotherms {1/(bound fraction of drug) vs. 1/[lipid]} were linear and K values were determined from their slopes by the method of linear least squares analysis. A computer program based on the $K=[A_B]/[A_F][L]$ relationship was written to predict bound drug levels for specified values of K and total drug.

Figure 2:
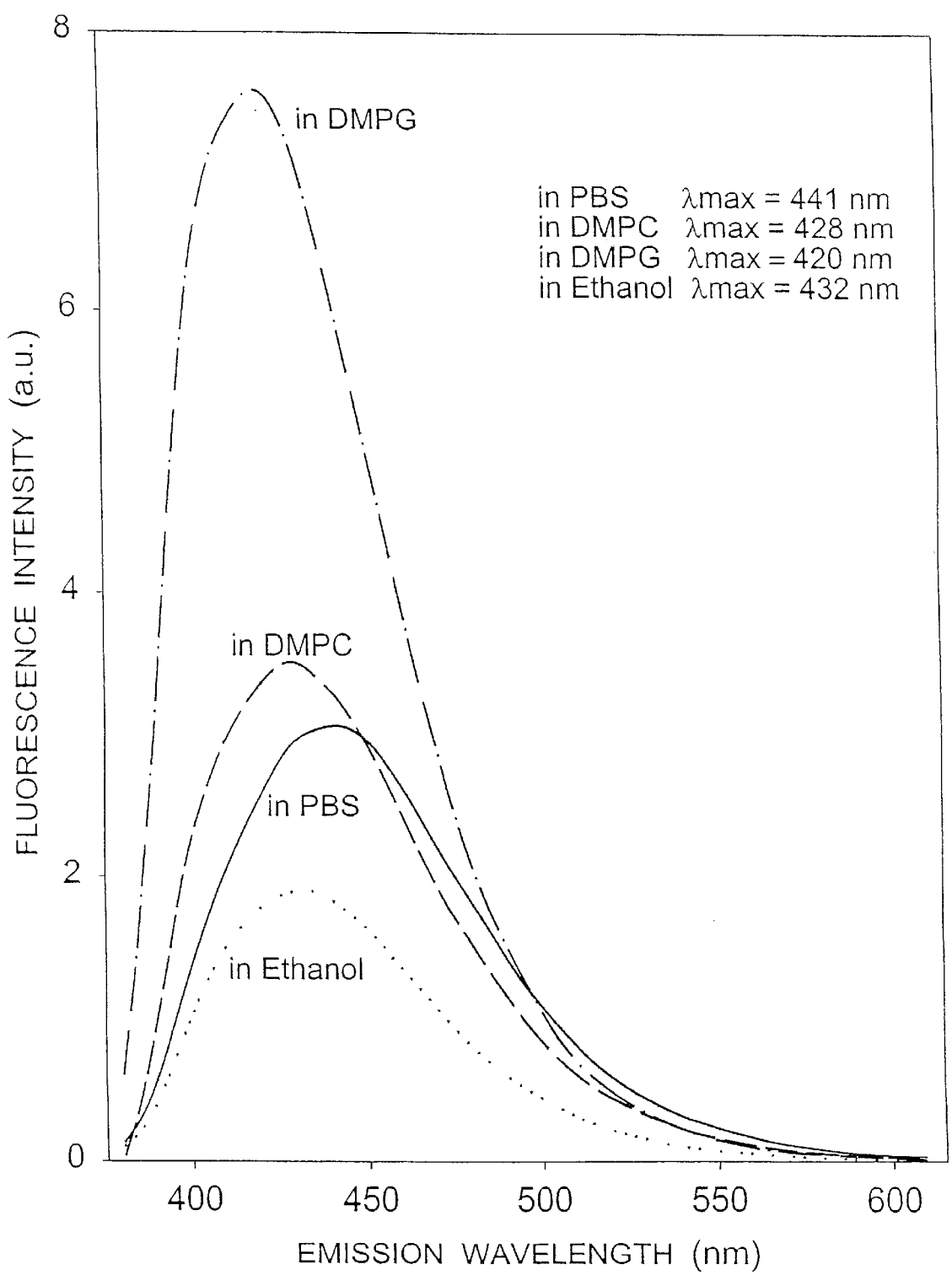
FIG. 2 is the fluorescence emission spectra of 4 μM of 7-[N-(4-methyl-1-piperazino) aminomethyl]-(20S)-camptothecin (CT-17) in various solvents and suspensions such as phosphate buffered saline, ethanol, and phosphate buffered saline containing small unilamellar vesicles (SUVs) composed either of DMPC or DMPG. Experiments were conducted at 37° C. using exciting light of 370 nm. Note that in the presence of liposomes composed of either DMPC or DMPG the fluorescence emission spectra of CT-17 increases in intensity and shifts to shorter wavelength, indicative of drug interaction with the membranes (lipid concentration 0.04M, λex=370 nm, EX resolution 8 nm, EM resolution 4 nm, without EM polarizer, HV=830V).

Fluorescence Anisotropy Titration and HPLC-Based Stability Assays Demonstrate that the New Polyamine Camptothecin Analog 7-[N-(4-methyl-1-piperazino)aminomethyl]-(20S)-camptothecin (CT-17) Displays Reduced Interactions with Lipid Vesicles Relative to the Prior Art Compound 7-(1-Aminoethyl)camptolthecin (7AEC). FIGS. 1 and 2 depict the fluorescence emission spectra of several of the new camptothecin analogs.

FIG. 1 summarizes the emission spectra of 1 $\mu$M 7-(1-aminoethyl)camptothecin (7AEC) in phosphate buffered saline solution. The figure indicates that upon introduction of lipid bilayers into the sample there is an increase in the fluorescence emission of the compound, indicative of an interaction between the drug and the membrane. Upon changing the solvent to ethanol the fluorescence also changes, with a decrease in the maximum fluorescence intensity. FIG. 2 summarizes the emission spectra of CT-17 in the presence and absence of membranes. In the case of CT-17 there is an increase in fluorescence intensity as the drug partitions into the lipid bilayer. In each case there is also a blue-shifting or shift in the emission spectra to lower wavelength upon drug interaction with membrane. The spectral data presented in FIGS. 1 and 2 clearly indicate that both agents are fluorescent and the spectral parameters of the drugs change upon addition of lipid bilayer membranes to the samples.

The intrinsic fluorescent nature of the camptothecins allows for the sensitive method of steady-state fluorescence anisotropy titration to be employed to determine the strength of the binding interactions of the various analogs with lipid bilayers. A steady-state fluorescence anisotropy (a) measurement is related to the rotational rate of the fluorescent molecule through the Perrin Equation:

$$a_o/a=1+(\tau/\phi)$$

where $a_o$ is the limiting fluorescence anisotropy in the absence of depolarizing rotations, $\tau$ is the excited-state lifetime, and $\phi$ is the rotational correlation time of the fluorophore. The above equation states that changes in either the $\tau$ or $\phi$ values of a fluorescent compound can modulate its steady-state anisotropy.

We have examined the excited-state lifetime values of camptothecin in PBS, glycerol, and methanol at 37° C. The lifetime values were determined to be 4.7 ns, 3.8 ns, and 3.5 ns, respectively. Similarly, we measured camptothecin's lifetime value when associated with DMPC bilayers at 37° C., and the average value for membrane-bound drug was found to be 3.7 ns.

Thus the lifetime measurements described above indicate that camptothecin's excited-state lifetime is relatively insensitive to alterations in microenvironment (e.g. a change in solvent or fluorophore relocation from an aqueous milieu to a phospholipid membrane). For a fluorophore whose $\tau$ value remains relatively constant during a transition which strongly impacts on its rotational motion (such as a change in solvent viscosity or fluorophore binding to large macromolecular assemblies such as liposomal particles), the Perrin equation indicates a direct relationship between a and $\phi$ values will exist (i.e. as the $\phi$ value of the fluorescent compound increases, then so too does its steady-state anisotropy value).

Previously we have shown that steady-state fluorescence anisotropy values of the camptothecin analogs are highly sensitive to solvent viscosity and to associations with small unilamellar lipid vesicles. For example, topotecan has an a value of 0.008 in PBS, but its value increases 9-fold and 40-fold in the viscous solvents octanol and glycerol, respectively. A 21-fold enhancement in the a value of camptothecin is observed upon binding of drug to vesicles composed of either DMPC or DMPG. Because of the sensitivity of the anisotropy value of the camptothecin drugs to membrane associations, we employed the method of fluorescence anisotropy titration to study the equilibrium binding of camptothecin analogs with lipid bilayers. The experiment consisted of determining the a values for a set of samples where the drug concentration in each was held constant (typically 1 or 2 μM), while the lipid concentration among the members of a set was varied from 0 to 0.29 M.

Figure 3:
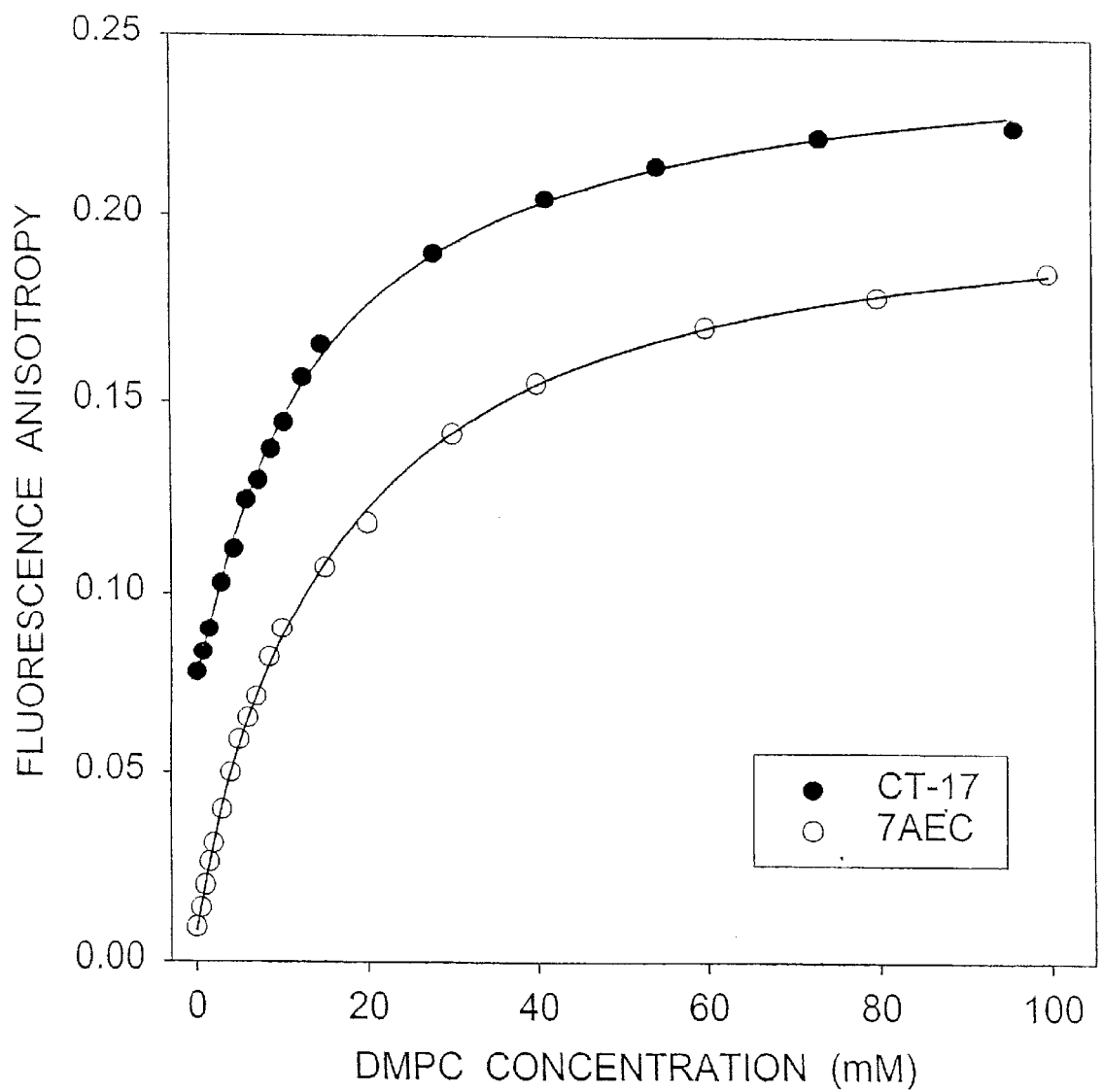
FIG. 3 is a study of the binding of 2 μM amounts of 7-(1-Aminoethyl)camptothecin (7AEC) or 7-[N-(4-methyl-1-piperazino) aminomethyl]-(20S).-camptothecin (CT-17) (prepared in Example 18) to small unilamellar vesicles composed of electroneutral DMPC suspended in phosphate buffered saline. Experiments were conducted at 37° C. using exciting light of 370 nm. Note that in the presence of increasing amounts of liposomes the drug anisotropy values increase until the majority of drug is liposome-bound. Analysis of the data reveals that the novel CT-17 agent has reduced membrane binding associations relative to the 7AEC molecule (data analysis is carried out in FIG. 5).
Figure 4:
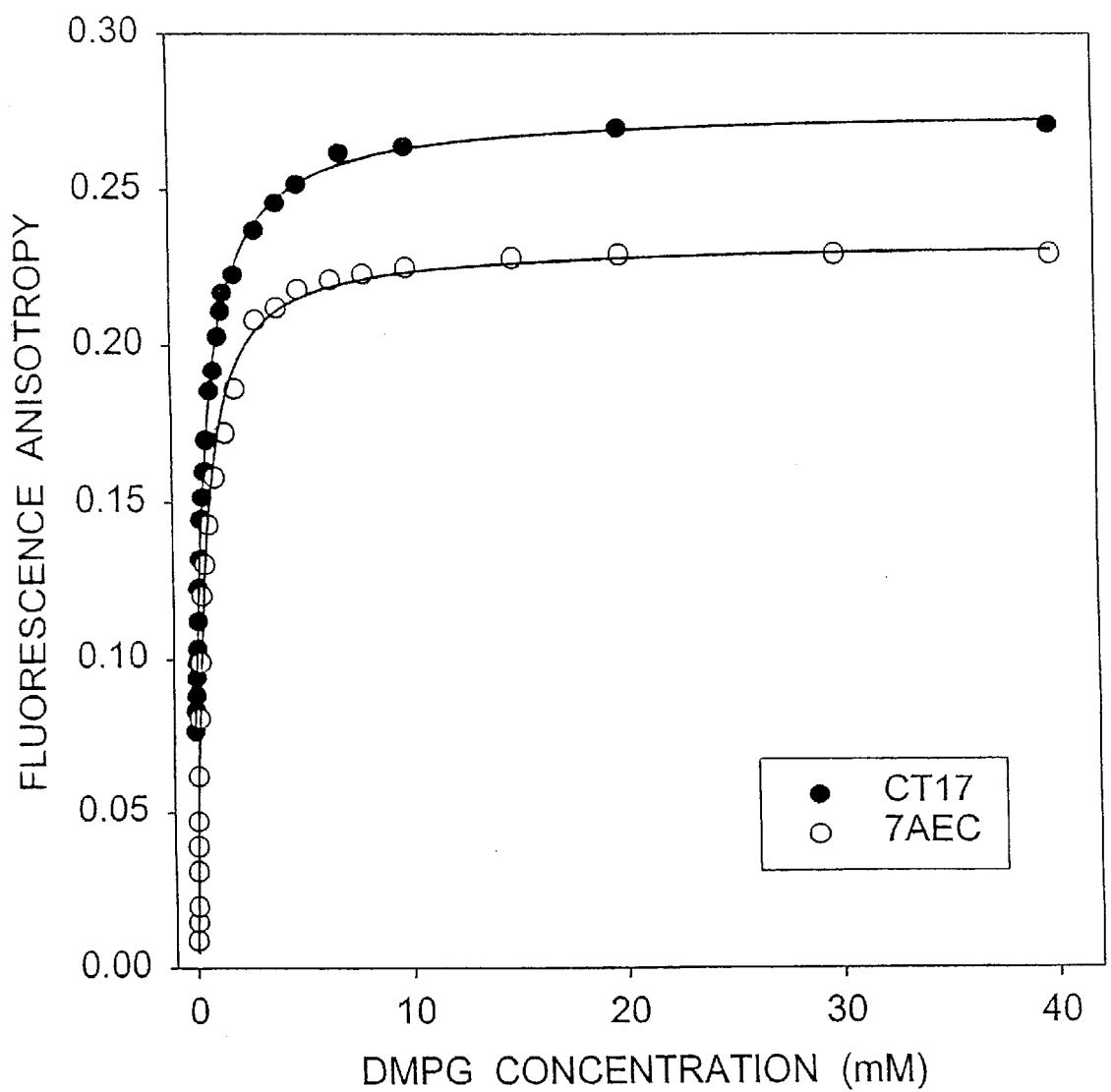
FIG. 4 is a study of the binding of 2 μM amounts of 7-(1-Aminoethyl)camptothecin (7AEC) or 7-[N-(4-methyl-1-piperazino) aminomethyl]-(20S)—camptothecin (CT-17) to small unilamellar vesicles composed of negatively-charged DMPG suspended in phosphate buffered saline. Experiments were conducted at 37° C. using exciting light of 370 nm. Note that in the presence of increasing amounts of liposomes the drug anisotropy values increase until the majority of drug is liposome-bound. Analysis of the data reveals that the novel CT-17 agent has reduced membrane binding associations for DMPG relative to the previously described 7AEC molecule (data analysis is carried out in FIG. 6).
Figure 5:
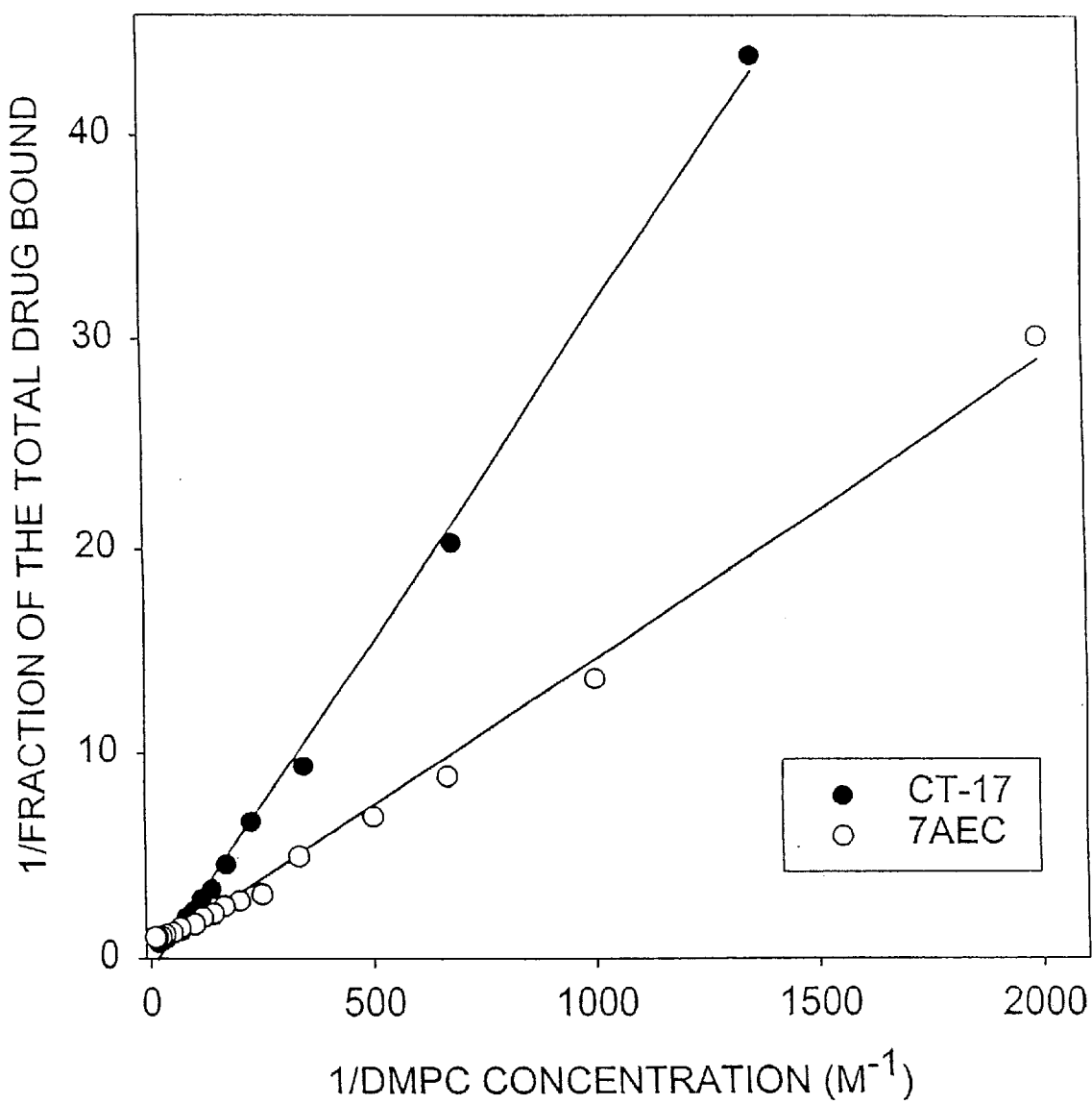
FIG. 5 shows double-reciprocal plots for the binding of 7-(1-Aminoethyl)camptothecin (7AEC) or 7-[N-(4-methyl-1-piperazino) aminomethyl]-(20S)-camptothecin (CT-17) to small unilamellar vesicles composed of electroneutral DMPC suspended in phosphate buffered saline (PBS), pH 7.4. Experiments were conducted at 37° C. using exciting light of 370 nm.
Figure 6:
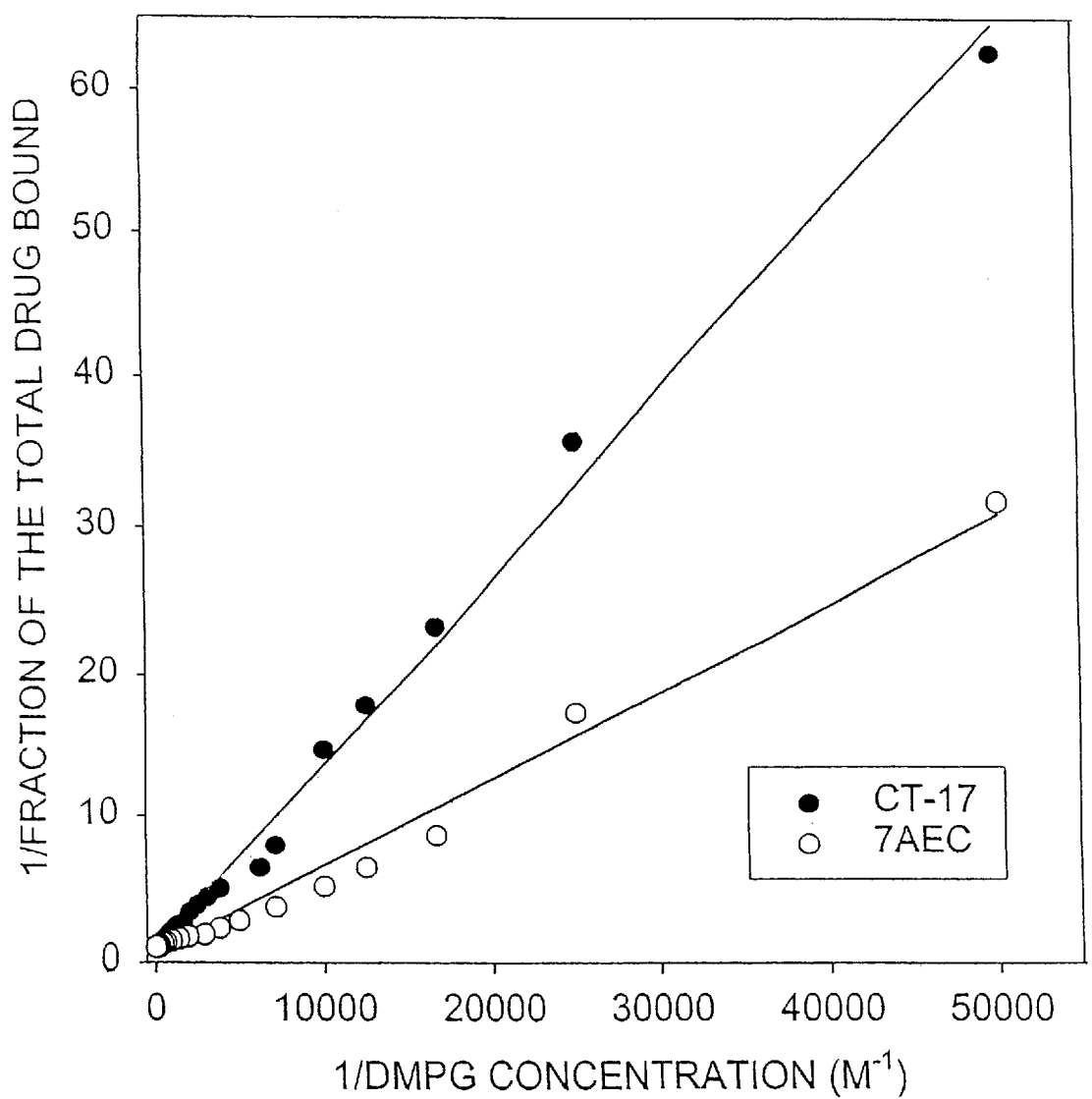
FIG. 6 shows double-reciprocal plots for the binding of 7-(1-Aminoethy)camptothecin (7AEC) or 7-[N-(4-methyl-1-piperazino) aminomethyl]-(20S)-camptothecin (CT-17) to small unilamellar vesicles composed of negatively-charged DMPG suspended in phosphate buffered saline, pH 7.4.

As a consequence of the fluorescence emissions from the 7AEC and CT-17 compounds, the adsorption isotherms summarized in FIGS. 3 and 4 were relatively free from any background signal. Using drug concentrations of 1 μM and long pass filters to isolate emitted light from background signal (i.e. scattered exciting light and extraneous fluorescence signal due to the possible presence of impurities), signal levels from drugs dissolved in PBS buffer were typically 99.97% in the absence of membrane and greater than 98% in the presence of membrane. Adsorption isotherms were used to determine overall association constants for the camptothecin drugs. Overall association constants are defined as:

$$K=[A_B]/[A_F][L]$$

where $[A_B]$ represents the concentration of bound drug, $[A_F]$ represents the concentration of free drug, and $[L]$ represents the total lipid concentration in the vesicle suspension. This equation is valid when the concentration of free lipid is approximately equal to the concentration of total lipid (i.e., the concentration of free lipid is in significant excess over the concentration of bound drug). Provided this condition is satisfied, K may be determined from the inverse of the slope of a double reciprocal plot. In such a double reciprocal plot (representative data are shown in FIGS. 5 and 6), 1/fraction of the total drug bound is plotted vs. 1/lipid concentration, with a y-intercept value of 1 (for a system displaying binding site homogeneity). Such double-reciprocal plots for the associations of the new camptothecin analogs with DMPC and DMPG small unilamellar vesicle (SUV) preparations were linear with good correlation coefficients. The linearity of these plots, as well as the corresponding plots for drug associations with other types of membrane preparations, indicates that fluorophore binding at these lipid concentrations is adequately described by the above equation.

The contents of Table 1 examine the structural basis of camptothecin associations for lipid bilayers. Two types of membrane were included in our studies which were conducted under near physiological conditions of pH and temperature; these membranes include fluid-phase and electroneutral L-α-dimyristoylphosphatidylcholine (DMPC); and fluid-phase and negatively-charged L-α-dimyristoylphosphatidylglycerol (DMPG). DMPC and DMPG have identical chain length but the charge on their head groups differ.

Table 1 clearly demonstrates how substitution of a polyamine at position 7 decreases equilibrium membrane associations relative to a prior art monoamino compound 7-(1-aminoethyl)camptothecin (7AEC). For electroneutral DMPC membranes CT-17 displays a greater than 2-fold reduction in membrane binding relative to the prior art monoamino compound 7AEC, while the corresponding reduction in binding for CT-17 interacting with negatively-charged membranes is three-fold relative to the 7AEC compound. This reduction in binding is a very favorable characteristic in situations where the drug is to be actively loaded into liposomes. The reduced membrane interactions will be a favorable characteristic with respect to drug retention within the particle.

TABLE 1

Overall association constants for camptothecin analogs interacting with unilamellar vesicles of electroneutral DMPC and negatively-charged DMPG in PBS buffer at pH 7.4 at physiological temperature.

| Compound | $K_{DMPC\ (M)}^{-1}$ | $K_{DMPG\ (M)}^{-1}$ |
| --- | --- | --- |
| Camptothecin | 100 | 100 |
| 7AEC | 75 | 2,000 |
| CT-17 | 30 | 800 |

To further study the differential interactions of CT-17 versus 7AEC with liposomal particles, high performance liquid chromatographic (HPLC) methods were employed to study drug stabilities in the absence and presence of membranes. In these experiments, small unilamellar vesicles (SUV) composed of dimyristoyl phosphatidylcholine (DMPC) were prepared by weighing out dry lipid powder (Avanti Polar Lipids) in a glass tube with screw cap top. The lipid was suspended in phosphate buffered saline, pH 7.4, at the concentration of 20 mg/ml and vortexed vigorously for 1 minute. The suspension was sonicated in a bath-type sonicator (Laboratory Supplies Co., Hicksville, N.Y.) for 2–4 hours until optically clear solution is obtained. This results in the formation of SUV. A decrease in pH from 7.4 to 7.2 was observed. The pH of the SUV preparation was adjusted to 7.4 by the addition of 0.1 M potassium hydroxide. The sample was resonicated after pH adjustment until optically clear. Small unilamellar vesicles composed of dimyristoyl phosphatidylglycerol (DMPG) were also prepared by weighing out dry powder of the lipid (Avanti Polar Lipids) in a glass tube with screw-cap top and prepared as in the case of DMPC. The pH of the preparation decreased from 7.4 to 6.9 and was adjusted to 7.4 by the addition of 0.1 M KOH. The preparation was resonicated for 30 minutes until optically clear.

Stock solutions of 7-(1-Aminoethyl)camptothecin, a monoamine compound known in the prior art, and CT-17 as prepared in Example 18 were prepared by weighing out dry powder and dissolving in dimethylsulfoxide (DMSO) at a concentration of 2 mM. The SUV preparations from above were incubated at 37° C. in a water bath for 30 minutes. The two camptothecin drugs were added to the SUV preparations such that the final drug concentrations were 1 μM. The samples were incubated at 37° C. and aliquots were withdrawn at 1 hour and 3 hours and added to cold methanol (−20° C.) and immediately analyzed by reversed-phase HPLC using the conditions as follows. Analysis was performed using either Waters Alliance 2690 LC system equipped with temperature controlled autosampler or Waters LC system equipped with temperature controlled 717 plus Autosampler and 501 pumps. The detection was using either Waters 470 or 474 fluorescence detectors. Solvent A was 2% triethylammonium acetate, pH 5.5 and Solvent B was acetonitrile. The column used was Waters Symmetry $C_{18}$, 5 μm (3.9×150 mm). The autosampler temperature was maintained at 4–5° C. The conditions used for analysis of 7-(1-Aminoethyl)camptothecin: Isocratic elution using 15% of solvent A and 85% of solvent B; detection using $\lambda_{ex}$=370 and $\lambda_{em}$=440. The conditions used for analysis of CT-17: Isocratic elution using 18.5% solvent A and 81.5% solvent B; detection using $\lambda_{ex}$=365 and $\lambda_{em}$=426. All the analyses were performed in triplicates. The HPLC data was collected and analyzed using Waters Millenium chromatography manager.

Table 2 (below) shows the percent of camptothecin drug in the active lactone form after both one hour and three hours of incubation in the presence of different lipids (components of liposomes) in phosphate buffered saline (PBS, pH 7.4) at 37° C. Extensive interaction of a camptothecin with lipid will result in higher percentage of lactone component present over longer periods. Table 2 indicates that the CT-17 camptothecin drug of the present invention has 20% less lactone at 1 hr and 17% less lactone at 3 hr compared to the prior art monoamine in the presence of DMPC, an electroneutral lipid. In the presence of a negatively charged lipid such as DMPG, CT-17 has 6% less lactone at 1 hr and 8% less lactone at 3 hr. These results are indicative of the desirable properties of these novel analogs including better water solubility, less membrane interaction and improved active loading into liposomal particles. Within the liposomal particle the CT-17 drug will prefer to reside in its active lactone form because of the reduced pH within the particle and because of the ability of the drug to self-associate at the higher drug concentrations within the particle.

Reduced albumin interactions will result in higher activity since the inactive carboxylate form of the drug will have less interaction with major blood protein albumin. Also, when actively loaded in liposomes, these new compounds of the present invention can be expected to be in the liposomal compartment and will not cross the lipid bilayer making them ideal for slow release drug delivery.

TABLE 2

Lipid (SUV)/Drug Interaction analyzed by HPLC
Percentage of Lactone

| | DMPC | | DMPG | |
|---|---|---|---|---|
| | 1 Hr | 3 Hr | 1 Hr | 3 Hr |
| a) 7AEC | 54 ± 0.3 | 36 ± 0.04 | 93 ± 0.3 | 86 ± 0.3 |
| b) CT-17 | 34 ± 3.0 | 19 ± 3.0 | 87 ± 2.0 | 78 ± 3.0 |

Lactone Ring Stability of Actively Loaded CT-17 Liposomes is Significantly Greater in PBS, Human Plasma, and Human Blood Than For Free Drug.

To determine the ability of CT-17 to be retained in liposomal preparations, the agent was loaded into liposomes using the active loading methodology as described previously (U.S. Pat. No. 5,192,549). Two types of liposomes were used: 1) non-stealth liposomes and 2) stealth liposomes. The liposome preparations were then incubated in various biological fluids to determine drug retention in the particle. In these experiments the lipid distearoylphosphatidylcholine (DSPC) was obtained from Avanti Polar Lipids (Birmingham, AL) and cholesterol was from Nutritional Biochemicals Corp., Cleveland, Ohio. For liposomal preparations that do not remain in circulation for long periods of time, the method of liposomal preparation first involved weighing DSPC (100 mg, 126.7 µmol) and cholesterol (25 mg, 65 µmol) in a round bottom flask followed by dissolution in 5 ml of chloroform. Solvent was evaporated at 55–60° C. on rotary evaporator for 15 min to form the lipid film. The residual solvent was then removed under high vacuum at room temperature overnight. The lipid film was hydrated using 5 ml of 0.1 M ammonium sulfate. MLVs were formed by shaking and occasional vortexing at 55–60° C. LUVs were formed by passing the liposome suspension through two 100 nm stacked polycarbonate filters under 20 psi pressure of nitrogen using 11 passes at 55–60° C. (Liposo-Fast-Pneumatic from AVESTIN, Toronto, Canada).

An ammonium ion gradient was established by passing 3 ml of a liposomal preparation through gel filtration columns (Econo-Pac 10DG, 10 ml, Bio-Rad) equilibrated with 0.15 M sodium chloride. The column was then eluted with 4 ml of 0.15 M sodium chloride. The size of the non-stealth lipid particle preparation was then evaluated using a Malvern Zetasizer 3000.

CT-17 was actively loaded by adding 1.006 mg (2.1 µmol) dissolved in 0.1 ml of 0.15 M NaCl to 1 ml of liposomal preparation and incubating at room temperature overnight. Free CT-17 was removed by passing the samples through 500 mg (dry weight) of DOWEX 50WX4-400, sodium form (Sigma). CT-17 encapsulated was quantitated by HPLC assay for CT-17. Non-stealth liposomal samples were extracted in methanol prior to analysis.

For the evaluation of drug encapsulation levels, HPLC assays were conducted on a Waters Alliance 2690 liquid chromatograph system equipped with temperature controlled auto-sampler. Elution from the column was monitored by a Waters 467 fluorescence detector using $\lambda_{ex}$=365 nm and $\lambda_{em}$=426 nm. The solvent system used was 18.5% solvent A and 81.5% solvent B; where solvent A was acetonitrile and solvent B was 2% triethylammonium acetate, pH 5.5. A Waters Symmetry $C_{18}$ column (5 µm, 150×39 mm) was used. The flow rate was 1 ml/min. CT-17 lactone form eluted with a retention time of 6.9 min and carboxylate form eluted with a retention time of 2.7 min. Our analyses indicated that the efficiency of the active loading process was 75% encapsulation, with a drug: lipid ratio of 1:20 an average particle size of 123 nm.

The novel CT-17 analog was also formulated in long-circulating or stealth liposomes that contained a polyethylene glycol (PEG) surface coating. These types of liposomal particles containing a polymer coating are often referred to as "Stealth" liposomes because of their ability to avoid opsonization and macrophage-mediated removal from the circulatory system. To generate long-circulating liposomes containing CT-17, the following materials were used: DSPC obtained from Avanti Polar Lipids (Alabaster, AL), M-DSPE-PEG-2000 obtained from Shearwater Polymers, Inc., Huntsville, Ala., and cholesterol from Nutritional Biochemicals Corp., Cleveland, Ohio. For the preparation of long-circulating liposomes, DSPC (83.7 mg, 106 µmol), M-DSPE-PEG-2000 (25.6 mg, 9.3 µmol) and cholesterol (27.3 mg, 70.7 µmol) were weighed in a round bottom flask and dissolved in 3 ml of chloroform and 2 ml of methanol. The molar ratio of DSPC/DSPE-PEG/Cholesterol was 5.7/0.5/3.8. The solvent was evaporated at 55–60° C. on rotary evaporator for 15 min to form the lipid film. The residual solvent was removed under high vacuum at room temperature overnight. Following the drying step, the lipid film was hydrated using 5 ml of 0.1 M ammonium sulfate. MLVs were formed by shaking and occasionally vortexing at 55–60° C. LUVs were then formed by passing the multilamellar liposome suspension through two 100 nm stacked polycarbonate filters under 25 psi pressure of nitrogen using 11 passes at 55–60° C. (Liposo-Fast-Pneumatic from AVESTIN, Toronto, Canada).

An ammonium ion gradient was established by passing 2.8 ml of liposomal preparation through a gel filtration column (Econo-Pac 10DG, 10 ml, Bio-Rad) equilibrated with 0.15 M sodium chloride followed by an elution step utilizing 3.5 ml of 0.15 M sodium chloride. The size of the long circulating lipid particles was determined using a Malvern Zetasizer 3000.

CT-17 was actively loaded by adding 0.457 mg (0.998 µmol) to 500 µl of liposomal preparation and incubating at room temperature overnight. Free CT-17 was removed by passing the samples through 200 mg (dry weight) of DOWEX 50WX4-400, sodium form (Sigma). The amount of CT-17 encapsulated within the liposomes was quantitated by a HPLC assay with CT-17 as analyte. Long-circulating liposomal samples were extracted in methanol prior to analysis. For the determination of the drug levels contained in the liposome preparations, the HPLC assay described above for the non-stealth liposomal preparations was used. The HPLC results indicated that the active loading process proceeded with 62.6% of the CT-17 being encapsulated into the PEG-coated liposomes with a drug:lipid ratio of 1:23.8. The particle size was 129 nm.

Figure 7:
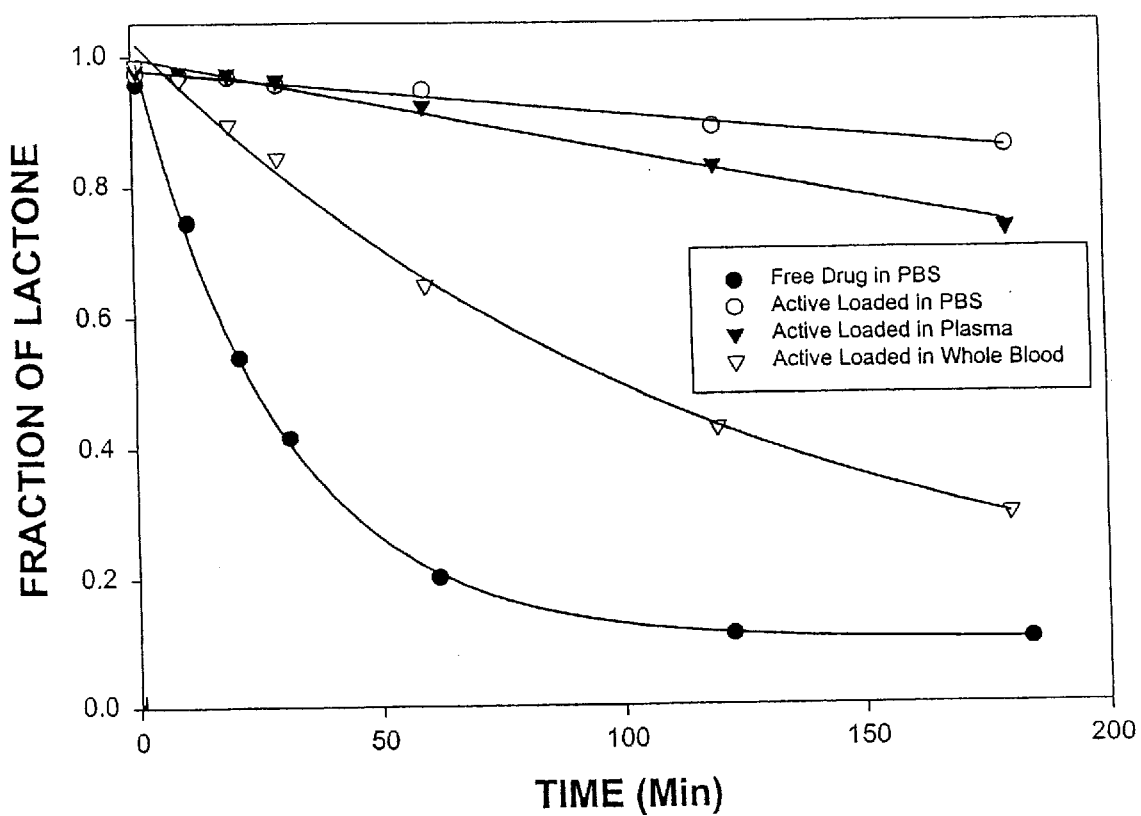
FIG. 7 is a graphical representation indicating the stabilization of the active lactone form of the drug CT-17 within liposomal particles in phosphate buffered saline (PBS), plasma and whole blood versus free drug in PBS. The liposomal particles studied in this experiment did not have a coating of polyethyleneglycol (PEG) on the surface of the particle as was the case for the liposomal preparation characterized in FIG. 8.

FIG. 7 is a graphical comparison of the stability of the lactone form of the camptothecin drug CT-17 as a function of time. Data are also presented in FIG. 7 for solutions where either the free form of CT-17 or an actively-loaded non-stealth liposomal form of CT-17 are added to phosphate buffered saline (PBS), plasma or whole blood. The 1.0 fraction of lactone represents that level that CT-17 would have optimal activity. Note particularly the high rate and extensive amount of hydrolysis of CT-17 free drug to inactive carboxylate that occurs in PBS solution. In contrast, the liposome stabilized CT-17 drug better retains its active lactone form in various media including PBS, plasma and whole blood. Advantageously, the amine groups in the CT-17 drug allow for active loading into the inner aqueous compartments of the liposomal particles. Further, the reduced bilayer association of the new CT-17 drug relative to other monoamine containing camptothecin drugs known in the art facilitates drug retention in the active lactone form within the liposomal particles.

Figure 8:
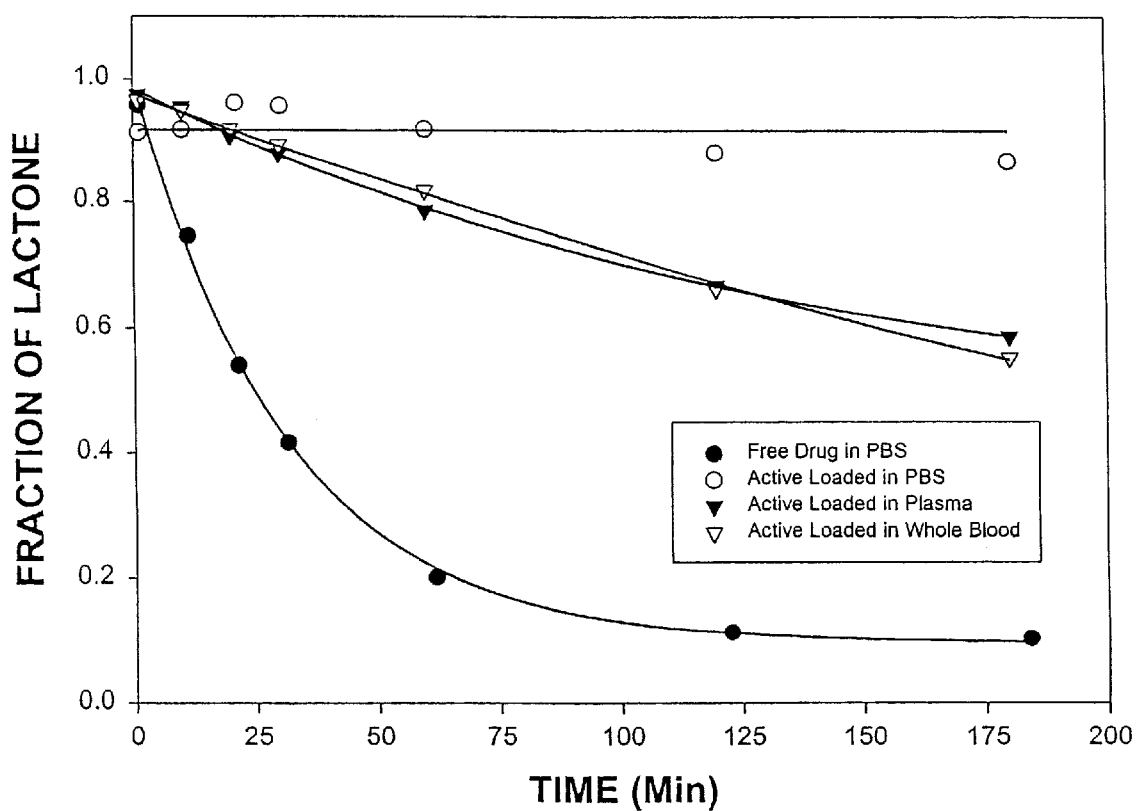
FIG. 8 is a graphical representation indicating the stabilization of the active lactone form of the drug CT-17 within liposomal particles in phosphate buffered saline (PBS), plasma and whole blood versus free drug in PBS. The liposomal particles studied in this experiment are long circulating or stealth liposomes containing a coating of polyethyleneglycol (PEG) on the surface of the particle.

FIG. 8 also depicts lactone stability data for CT-17 as a function of time. Data are also presented in FIG. 8 for solutions where either the free form of CT-17 or an actively-loaded PEG-coated liposomal form of CT-17 are added to phosphate buffered saline (PBS), plasma or whole blood. The 1.0 fraction of lactone represents that level that CT-17 would have optimal activity. As with the trend noted in the data in FIG. 7, there is a particularly high rate and extensive amount of hydrolysis of CT-17 free drug to inactive carboxylate that occurs in PBS solution. In contrast, the stealth liposomal preparations of CT-17 better retain the active lactone form in various media including PBS, plasma and whole blood. As before, the active loading into the inner aqueous compartments of the liposomal particles stabilizes the drug. Further, the reduced bilayer association of the new CT-17 drug relative to other monoamine containing camptothecin drugs known in the art facilitates drug retention in the active lactone form within the liposomal particles.

EXAMPLE 78

Figure 9:
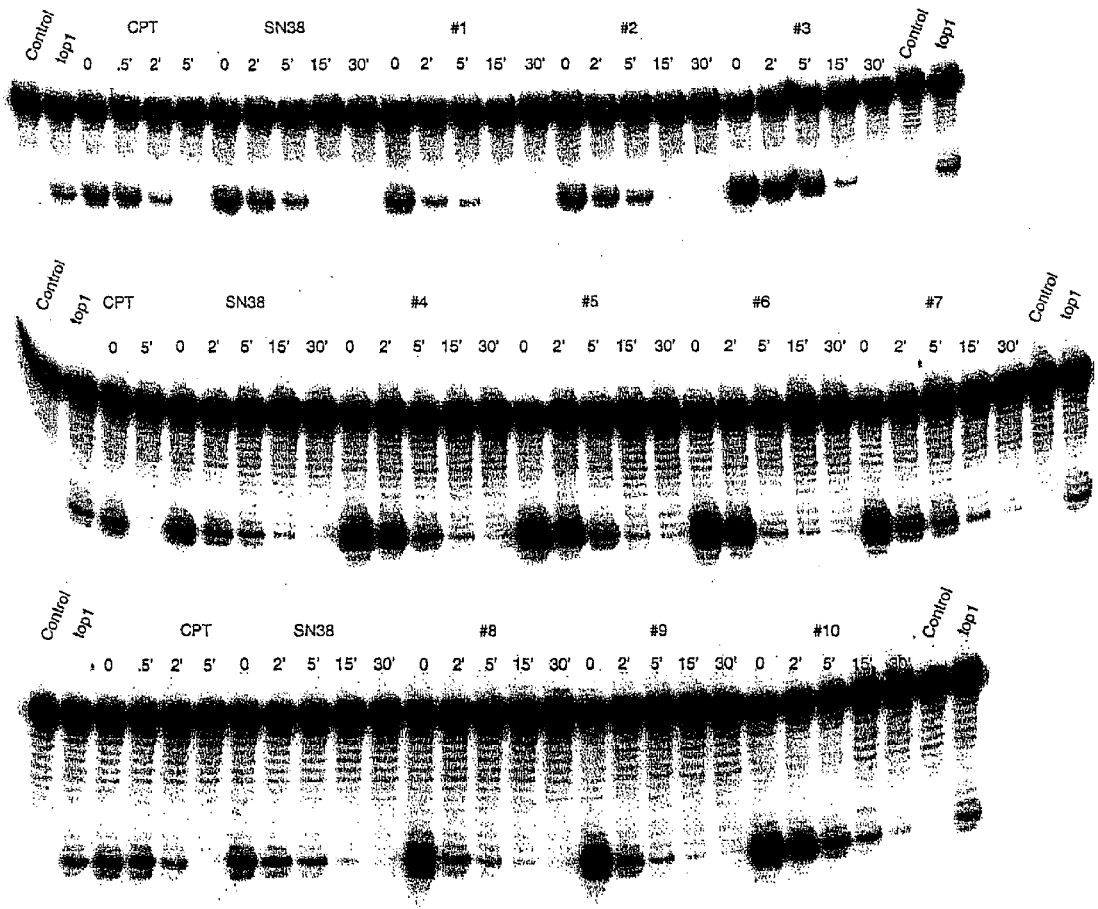
FIG. 9 is a typical phosphoimager picture showing the timecourse of the effects of various camptothecins on the relaxation of DNA in the presence of topoisomerase I. Topoisomerase I-mediated cleavage generates DNA fragments that can be readily detected by electrophoresis and quantitated by phosphoimager analysis. Note that several of the analogs of the current invention such as 7-(1-Guanidinopropyl)-20(S)camptothecin (lane#8) and 7-(1-Guanadinoethyl)-20(S)camptothecin (lane#9) are good inducers of cleavable complex formation and the distribution of cleavage sites are comparable to those generated by camptothecin or 7-ethyl-10-hydroxycamptothecin (SN-38).

Evaluation of the Relative Abilities of the Novel Polyamine Camptothecin Analogs to Induce Topoisomerase I Mediated DNA Single Strand Breaks. We have evaluated the abilities of the novel compounds of the present invention to inhibit the topoisomerase I enzyme. In these experiments the oligonucleotide was labeled at the 3'-end of the upper (scissile) strand with 32P-α-cordycepin and terminal transferase (Pommier, Y., Kohlhagen, G., Kohn, F., Leteurtre, F., Wani, M. C., and Wall, M. E. Proc. Natl. Acad. Sci. U.S.A. 92:8861–8865, 1995). Topoisomerase I (Top1) cleavage generates a 23mer that can be easily detected by electrophoresis and quantitated by Phosphorimager analysis. Tanizawa et al. (Tanizawa, A., Kohn, K. W., Kohlhagen, G., Leteurtre, F., and Pommier, Y. Biochemistry 43:7200–7206, 1995) have previously shown that camptothecin derivatives differ in the manner in which they stabilize the top1 cleavable complexes that they induce. The novel polyamine camptothecins of the present invention were compared in this assay. 0.35M NaCl was added to force top 1-mediated DNA religation and DNA cleavage was measured at various times after NaCl addition. FIG. 9 is a typical phosphoimager picture showing the timecourse of the effects of various camptothecins on the relaxation of DNA in the presence of topoisomerase I. Topoisomerase I-mediated cleavage generates DNA fragments that can be readily detected by electrophoresis and quantitated by phosphorimager analysis. Note that several of the analogs of the current invention such as 7-(1-Guanidinopropyl)-20(S)camptothecin (compound #8) and 7-(1-Guanadinoethyl)-20(S)camptothecin (compound #9) are good inducers of cleavable complex formation and the distribution of cleavage sites are comparable to those generated by camptothecin or 7-ethyl-10-hydroxycamptothecin (SN-38). FIG. 9 shows that cleavable complexes induced by SN-38 reversed more slowly than those induced by camptothecin. This slower reversal may correspond to more stable cleavable complexes. The guanadino polyamine compounds of the present invention (compounds 8 and 9) show cleavable complexes with intermediate stabilities between camptothecin and SN-38.

Figure 10:
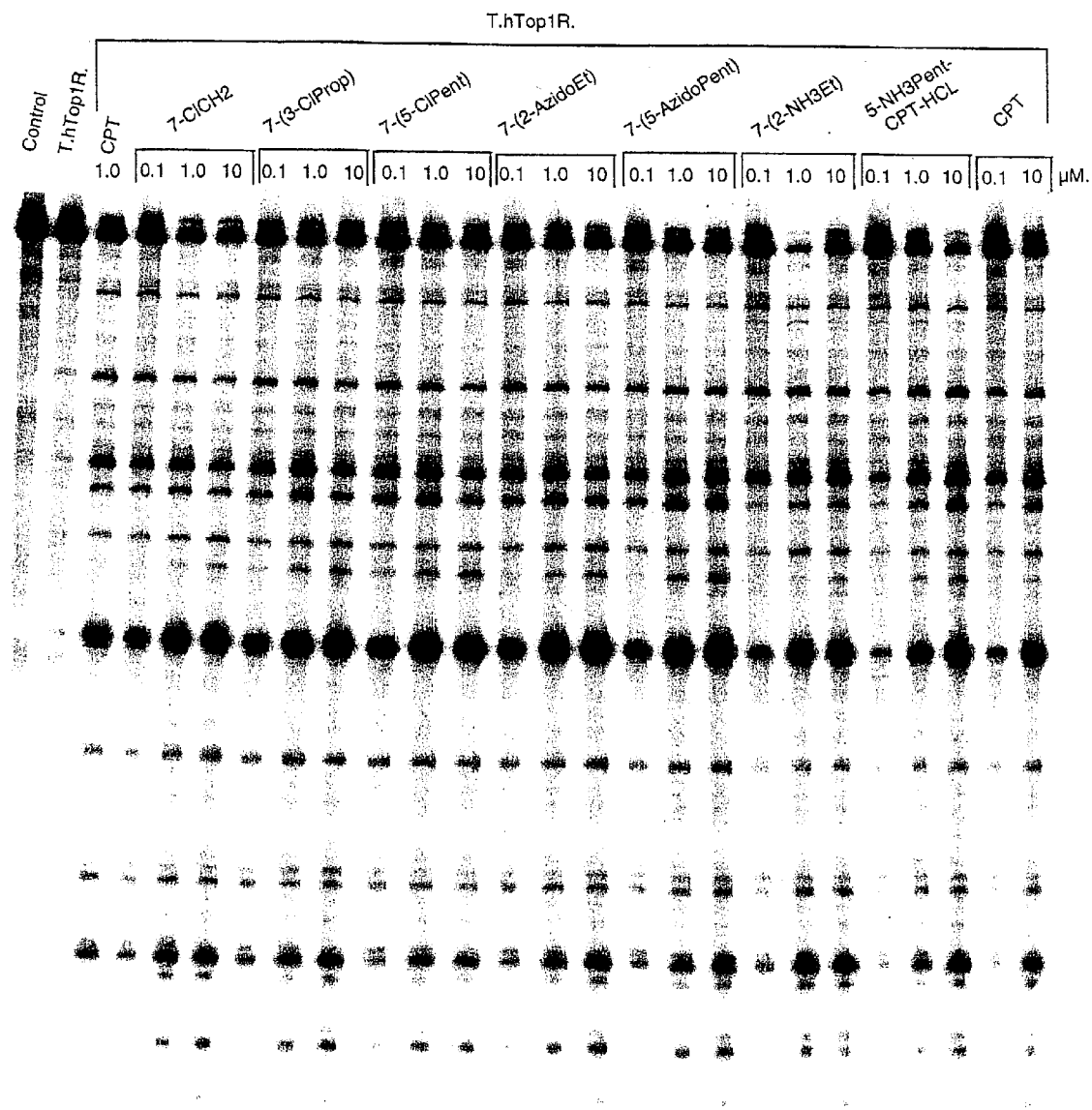
FIG. 10 is a phosphoimager picture showing the dose response of various camptothecin drugs on the relaxation of DNA in the presence of topoisomerase I. Topoisomerase I-mediated cleavage generates DNA fragments that can be readily detected by electrophoresis and quantitated by phosphoimager analysis as shown.

FIG. 10 is a phosphoimager picture showing the dose response of various camptothecin compounds described in the present invention on the relaxation of DNA in the presence of topoisomerase I. Topoisomerase I-mediated cleavage generates DNA fragments that can be readily detected by electrophoresis and quantitated by phosphorimager analysis as shown. The 7-(2-azidoethyl) and 7-(5-azidopentyl) analogs showed a particularly good dose response with respect to inducing DNA fragmentation.

Figure 11:
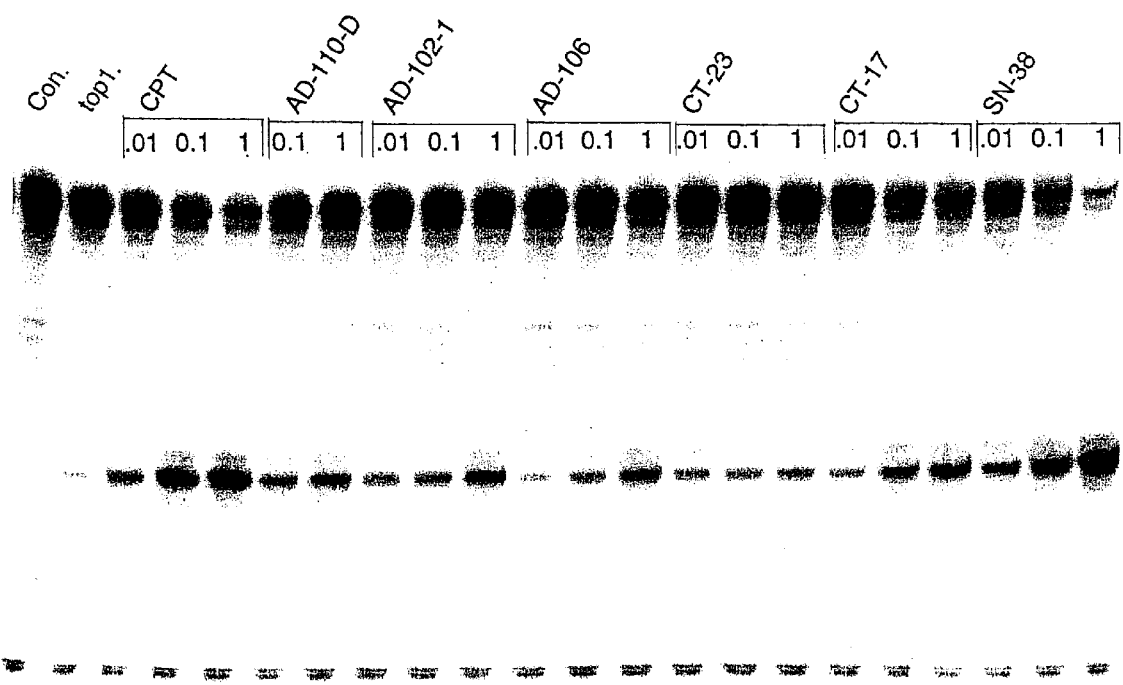
FIG. 11 contains a phosphoimager picture (bottom figure) showing the dose response effects of several of the novel polyamine camptothecin drugs of the current invention on the relaxation of DNA in the presence of topoisomerase I. Topoisomerase I-mediated cleavage generates DNA fragments that can be readily detected by electrophoresis and quantitated by phosphoimager analysis (top figure). Note that several of the analogs of the current invention such as 7-[N-(4-methyl-1-piperazino) aminomethyl]-(20S)-camptothecin (CT-1 7) are capable of inducing cleavable complex formation and the distribution of cleavage sites are comparable to those generated by camptothecin or 7-ethyl-10-hydroxycamptothecin (SN-38). Quantitation shows that the intrinsic potency of the CT-17 analog is somewhat less than the potencies of the camptothecin and SN-38 standards.

FIG. 11 contains a phosphoimager picture (bottom figure) showing the dose response effects of several of the novel polyamine camptothecins of the current invention on the relaxation of DNA in the presence of topoisomerase I. Topoisomerase I-mediated cleavage generates DNA fragments that can be readily detected by electrophoresis and quantitated by phosphorimager analysis (top figure). Note that several of the analogs of the current invention such as 7-[N-(4-methyl-1-piperazino) aminomethyl]-(20S)-camptothecin (CT-17) are capable of inducing cleavable complex formation and the distribution of cleavage sites are comparable to those generated by camptothecin or 7-ethyl-10-hydroxycamptothecin (SN-38). Quantitation shows that the CT-17 analog is somewhat less potent at promoting DNA cleavage relative to the camptothecin and SN-38 standards. Although the intrinsic potency of the CT-17 polyamine is slightly less than the camptothecin and SN-38 standards, CT-17 demonstrates a much better ability to be retained in liposomal carriers in the active form (FIGS. 7 and 8) and thus the ability of liposomal formulations to target tumors and deliver large amounts of the bioactive lactone form of CT-17 will more than compensate for any differences that exist in intrinsic potency.

Synthesis of new C-7 substituted homocamptothecins
Representative examples:
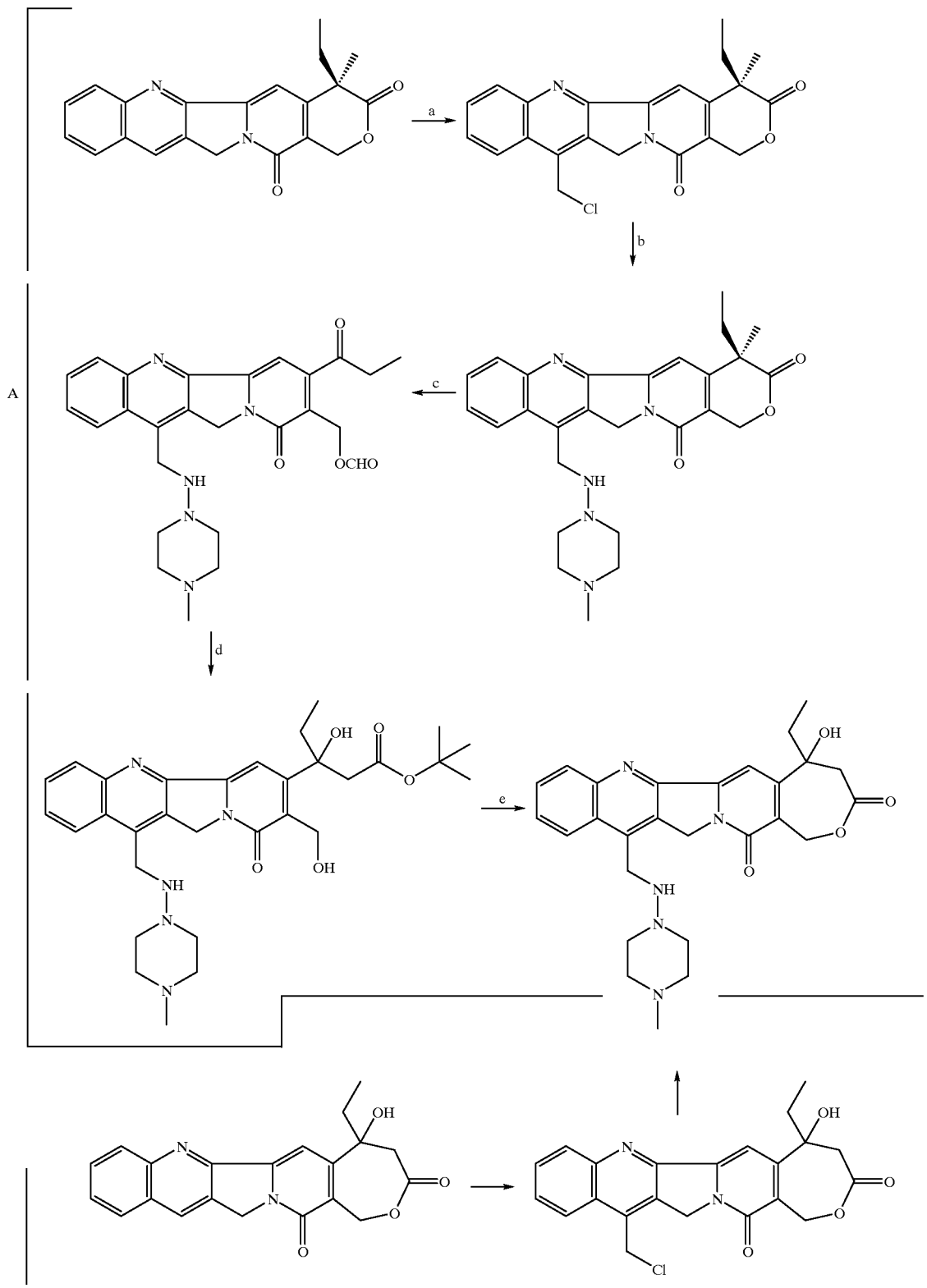

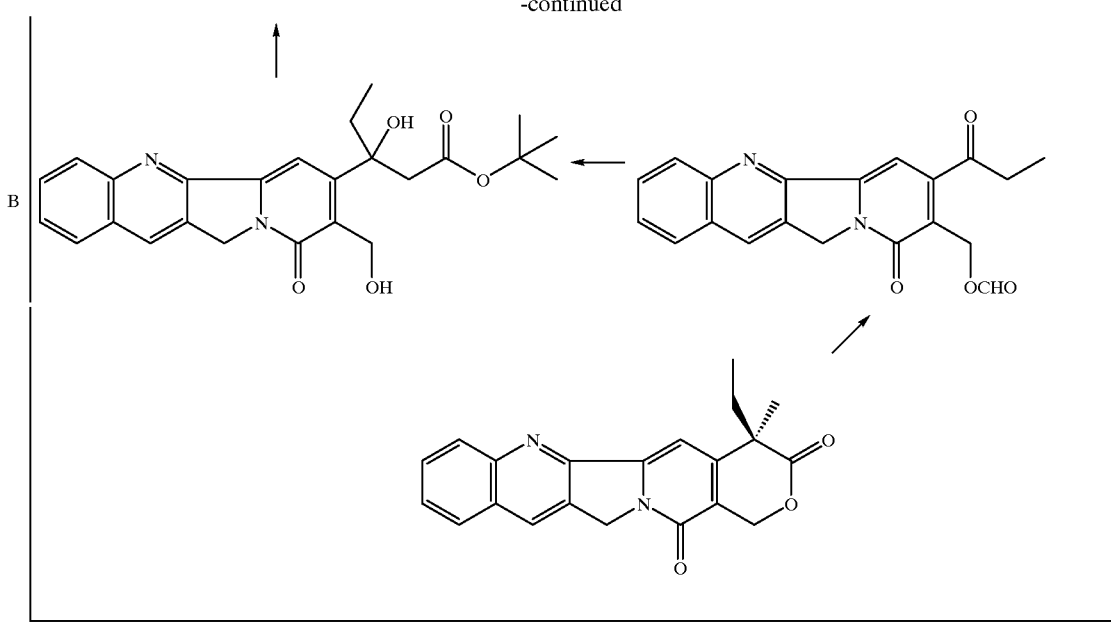

EXAMPLE 79

Synthesis of new C-7-substituted homocamptothecins (Route B). 7-Chloromethylhomocamptothecin To a suspension of homocamptothecin (3.12 g, 8.6 mmol, synthesized according to the published method; Bioor. Med. Chem. Lett. 1997, 7, 2235–2238) in a mixture of chloroacetaldehyde (18 ml) and $H_2O$ (75 ml). 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), organic layer was washed with brine and died over $MgSO_4$. Evaporation of the solvent gave brown oil. Purification of the crude product by column chromatography (eluent: Chloroform. methanol 98:2) furnished 2.98 g (85% yield) of the product. Mp>300° C. IR (KBr) 1650, 1760, $cm^{-1}$; $^1$H-NMR (DMSO-$d_6$) δ 0.85 (t, 3H), 1.85 (m, 2H), 3.31 (dd, 2H), 4.42 (s, 2H) 5.23 (s, 2H), 5.51 (dd, 2H), 6.01 (s, 1H), 7.72 (t, 1H), 7.85 (t, 1H), 8.22 (d, 1H), 8.16 (d, 1H), 8.71 (s, 1H); $^{13}$C-NMR (DMSO-$d_6$) δ 8.50, 36.45, 42.64, 50.48, 50.78, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. ($C_{22}H_{19}N_2O_4Cl$) 409.5.

EXAMPLE 80

7-(1-Chloropropyl)homocamptothecin

To a suspension of homocamptothecin (3.12 g, 8.6 mmol) in a mixture of 4-chlorobutanal (3 g, 30 mmol) and $H_2O$ (75 ml). 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), organic layer was washed with brine and died over $MgSO_4$. Evaporation of the solvent gave brown oil. Purification of the crude product by column chromatography (eluent: Chloroform: methanol 98:2) furnished 3.12 g (83% yield) of the product. Mp>300° C. IR (KBr) 1660, 1760, $cm^{-1}$; $^1$H-NMR (DMSO-$d_6$) δ 0.85 (t, 3H), 1.85 (m, 2H), 1.91 (m, 2H), 2.56 (m, 2H), 3.31 (dd, 2H), 3.38 (m, 2H) 5.23 (s, 2H), 5.52 (m, 2H), 6.11 (s, 1H), 7.62 (m, 1H), 7.85 (m, 1H), 8.13 (d, 1H), 8.26 (d, 1H), 8.71 (s, 1H); $^{13}$C-NMR (DMSO-$d_6$) δ 8.50, 32.90, 35.26, 36.45, 42.64, 44.61, 50.78, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. 437.5 ($C_{24}H_{23}N_2O_4Cl$)

EXAMPLE 81

7-(1-Chloropenthyl)homocamptothecin

To a suspension of homocamptothecin (3.12 g, 8.6 mmol) in a mixture of 6-chlorohexanal (6.9 g, 50 mmol) and $H_2O$ (75 ml). 75% $H_2SO_4$ (75 ml) was added dropwise, and then $FeSO_4 7H_2O$ (2.40 g, 8.6 mmol) was added. To the ice-cold mixture, 30% $H_2O_2$ (15 ml, 6.6 mmol) was added dropwise for 2 h with stirring. The mixture was stirred at room temperature for 14 h then diluted with $H_2O$, extracted with chloroform (3×200 ml), organic layer was washed with brine and died over $MgSO_4$. Evaporation of the solvent gave brown oil. Purification of the crude product by column chromatography (eluent: Chloroform: methanol 98:2) furnished 3.25 g ( 81% yield) of the product. Mp>300° C. IR (KBr) 1660, 1760, $cm^{-1}$; $^1$H-NMR (DMSO-$d_6$) δ 0.85 (t, 3H), 1.29–1.62 (m, 4H), 1.85 (m, 2H), 2.55 (m, 2H), 3.31 (dd, 2H), 3.34 (m, 2H) 5.23 (s, 2H), 5.52 (m, 2H), 6.11 (s, 1H), 7.62 (m, 1H), 7.85 (m, 1H), 8.13 (d, 1H), 8.26 (d, 1H), 8.71 (s, 1H); $^{13}$C-NMR(DMSO-$d_6$) δ 8.50, 27.02, 31.06, 33.01, 35.08, 36.45, 42.64, 45.12, 50.78, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. $C_{26}H_{27}ClN_2O_4$ (466.9)

EXAMPLE 82

7-[N-(2-(4-morpholino)ethyl)aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 2 ml of 4-ethylaminomorpholine in 20 ml of dry toluene. The reaction mixture was allowed to stir for 2 h after which the reaction mixture was concentrated to a thick residue under high vacuum followed by purification by column 15 chromatography using silica gel (CHCl$_3$/MeOH 95:5). The evaporation of solvent gave 111 mg (44%) of 7-N-(2-(4-morpholino)ethyl)methylamino homocamptothecin as a yellow solid. Mp 202–204° C. (d). IR (K Br) v: 1770, 1660, 1600 cm$^{-1}$. $^1$H-NMR (DMSO-d$_6$) δ 0.866 (t, 3H), 1.85 (m, 2H), 2.36–2.65 (m, 8H) 3.31 (dd, 2H), 3.81 (s, 2H) 5.23 (s, 2H), 5.51 (dd, 2H), 6.01 (s, 1H), 7.72 (t, 1H), 7.85 (t, 1H), 8.22 (d, 1H), 8.16 (d, 1H), 8.71 (s, 1H); $^{13}$C-NMR (DMSO-d$_6$) δ 8.55, 36.41, 48.82, 50.48, 50.78, 54.71, 55.82, 56.58, 61.34, 71.77, 73.56, 101.11, 122.59, 126.84, 128.25, 128.63, 129.11, 131.17, 131.77, 139.51, 145.16, 147.84, 152.66, 155.71, 160.11, 171.78. Anal. (C28H32N4O5) 505.2.

EXAMPLE 83

7-[N-(2-(1-Pyrrolidino) ethyl)aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 3 ml of 1-ethylaminopyrrolidine in 20 ml of dry toluene. The reaction mixture was allowed to stir for 2 h after which the reaction mixture was concentrated to a thick residue under high vacuum followed by purification by column chromatography using silica gel (CHCl3/MeOH, 90:10). The evaporation of solvent gave 107 mg (44%) of 7-[N(2-(1-Pyrrolidino) ethyl)methylamino] homocamptothecin as a yellow solid. Mp 212–214° C. (d). IR (KBr) 1650, 1760, cm$^{-1}$; $^1$H-NMR (DMSO-d$_6$) δ 0.85 (t, 3H), 1.61–1.85 (m, 6H), 2.20–2.65 (m, 8H), 3.31 (dd, 2H), 3.82 (s, 2H) 5.23 (s, 2H), 5.51 (dd, 2H), 6.01 (s, 1H), 7.72 (t, 1H), 7.85 (t, 1H), 8.22 (d, 1H), 8.16 (d, 1H), 8.71 (s, 1H); $^{13}$C-NMR (DMSO-d$_6$) δ 8.50, 23.24, 36.45, 48.64, 50.48, 50.78, 51.43, 54.71, 55.63, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. (C$_{28}$H$_{32}$N$_4$O$_4$) 489.2.

EXAMPLE 84

7-[N-(4-methyl-1-piperazino)aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 3 ml of 4-methylpiperazine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 90:10). The evaporation of solvent gave 107 mg (44%) of 7-[N-(4-methyl-1-piperazino) methylamino] homocamptothecin as a yellow solid. Mp 205– 207° C. (d). IR (KBr) 1650, 1760, cm$^{-1}$; $^1$H-NMR (DMSO-d$_6$) δ 0.83 (t, 3H), 1.86 (m, 2H), 2.24 (s, 3H), 2.45–2.70 (m, 8H), 3.33 (dd, 2H), 3.91 (s, 2H) 5.22 (s, 2H), 5.651 (dd, 2H), 6.07 (s, 1H), 7.68 (t, 1H), 7.81 (t, 1H), 8.12 (d, 1H), 8.14 (d, 1H), 8.70 (s, 1H); $^{13}$C-NMR (DMSO-d$_6$) δ 8.42, 36.45, 38.43, 55.62, 57.43, 46.69, 50.48, 50.77, 61.34, 73.56, 101.21, 122.59, 126.74, 128.21, 128.59, 129.21, 131.22, 131.78, 139.55, 145.18, 147.77, 152.56, 155.62, 160.21, 171.63. Anal. C$_{27}$H$_{31}$N$_5$O$_4$ (489.57).

EXAMPLE 85

7-[N-(2-(1-Piperidino) ethyl)aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 3 ml of 1-ethylaminopiperidine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 90:10). The evaporation of solvent gave 103 mg (41%) of 7-[N-(2-(1-Piperidino) ethyl)aminomethyl] homocamptothecin as a yellow solid. Mp 188–196° C. (d). IR (KBr) 1650, 1760, cm$^{-1}$; $^1$H-NMR (DMSO-d$_6$) δ 0.85 (t, 3H), 1.85 (m, 2H), 2.37–2.65 (m, 8H), 3.28 (dd, 2H), 3.65–3.81 (m, 6H), 3.86 (s, 2H) 5.32 (s, 2H), 5.53 (dd, 2H), 5.96 (s, 1H), 7.71 (t, 1H), 7.82 (t, 1H), 8.13 (d, 1H), 8.19 (d, 1H), 8.69 (s, 11H); $^{13}$C-NMR (DMSO-d$_6$) δ 8.41, 36.35, 48.81, 50.48, 50.78, 55.78, 56.51, 61.34, 71.78, 73.51, 101.22, 122.48, 126.74, 128.22, 129.03, 129.31, 131.13, 131.79, 139.58, 145.22, 147.80, 152.59, 155.68, 160.21, 171.82. Anal. C$_{21}$H$_{32}$N$_4$O$_5$ (502.5)

EXAMPLE 86

7-[N-(4-morpholino) aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 2 ml of 4-aminomorpholine in 20 ml of dry toluene. The reaction mixture was allowed to stir for 2 h after which the reaction mixture was concentrated to a thick residue under high vacuum followed by purification by column chromatography using silica gel (CHCl$_3$/MeOH, 95:5). The evaporation of solvent gave 90 mg (38%) of 7-[N-(4-morpholino) methylamino] homocamptothecin as a yellow solid. Mp 195–197° C. (d). IR (KBr) 1650, 1760, cm$^{-1}$; $^1$H-NMR (DMSO-d$_6$) δ 0.85 (t, 3H), 1.85 (m, 2H), 2.9 (m, 4H), 3.67 (m, 4H), 3.31 (dd, 2H), 3.91 (s, 2H) 5.23 (s, 2H), 5.51 (dd, 2H), 6.01 (s, 1H), 7.72 (t, 1H), 7.85 (t, 1H), 8.22 (d, 1H), 8.16 (d, 1H), 8.71 (s, 1H); $^{13}$C-NMR (DMSO-d$_6$) δ 8.50, 36.45, 50.48, 50.78, 54.71, 58.8, 61.34, 69.67, 73.56, 101.11, 122.59, 126.78, 128.25, 128.63, 129.11, 131.17, 131.77, 139.51, 145.16, 147.84, 152.66, 155.81, 160.11, 171.78. Anal.C27H29N4O5 (478.20)

EXAMPLE 87

7-[N-(4-hydroxymethyl-1-piperazino)aminomethyl] homocamptothecin:

To a dry 100 ml round bottom flask fitted with a magnetic stir bar was added 204 mg (0.5 mmol) of 7-chloromethylhomocamptothecin and 20 ml dry dimethylsulfoxide. The mixture was allowed to stir until all the solid was dissolved. To the remaining solution was added a solution of 3 ml of 4-hydroxymethylmethylpiperazine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 80:20). The evaporation of solvent gave 116 mg (46%) of 7-N-(4-hydroxymethyl-1-piperazino) aminomethyl] homocamptothecin as a yellow solid. Mp 187–190° C. (d). IR (KBr) 1640, 1750, cm$^{-1}$; $^1$H-NMR (DMSO-d$_6$) δ 0.86 (t, 3H), 1.85 (m, 2H), 2.48–2.65 (m, 8H), 3.31 (dd, 2H), 3.92 (s, 2H), 4.61 (s, 2H), 5.23 (s, 2H), 5.51 (dd, 2H), 6.11 (s, 1H), 7.70 (t, 1H), 7.85 (m, 1H), 8.22 (m, 1H), 8.16 (d, 1H), 8.71 (s, 1H); $^{13}$C-NMR (DMSO-d$_6$) δ 8.60, 36.45, 49.24, 50.48, 50.68, 54.71, 57.5, 61.34, 73.56, 76.61, 101.11, 122.59, 126.84, 128.25, 128.63, 129.11, 131.17, 131.77, 139.51, 145.16, 147.84, 152.66, 155.71, 160.11, 171.78. C$_{27}$H$_{31}$N$_5$O$_5$ (505.5).

EXAMPLE 88

7-[3-N-(2-(4-morpholino)ethyl)aminopropyl] homocamptothecin:

To a dry 100 ml round bottom flask fitted with a magnetic stir bar was added 218 mg (0.5 mmol) of 7-(1-chloropropyl) homocamptothecin and 20 ml dry dimethylsulfoxide. The mixture was allowed to stir until all the solid was dissolved. To the remaining solution was added a solution of 2 ml of 4-ethylaminomorpholine in 20 ml of dry toluene. The reaction mixture was allowed to stir for 2 h after which the reaction mixture was concentrated to a thick residue under high vacuum followed by purification by column chromatography using silica gel (CHCl$_3$/MeOH, 95:5). The evaporation of solvent gave 139 mg (43%) of 7-[3-N-(2-(4-morpholino)ethyl) aminopropyl] homocamptothecin as a yellow solid. Mp 194–196 C (d). IR (KBr) 1660, 1760, cm$^{-1}$; $^1$H-NMR (DMSO-d$_6$) δ 0.85 (t, 3H), 1.85 (m, 2H), 1.91 (m, 2H), 2.35–2.56 (m, 10H), 2.65 (m, 2H), 3.31 (dd, 2H), 3.67 (m, 4H), 5.23 (s, 2H), 5.52 (m, 2H), 6.11 (s, 1H), 7.62 (m, 1H), 7.85 (m, 1H), 8.13 (d, 1H), 8.26 (d, 1H), 8.71 (s, 1H); $^{13}$C-NMR (DMSO-d$_6$) δ 8.50, :32.90, 35.26, 36.45, 42.64, 48.81, 49.2, 50.78, 55.8, 56.5, 71.8, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. C35H47N6O6 (647.2).

EXAMPLE 89

7-[3-N-(2-(1-Pyrrolidino) ethyl)aminopropyl] homocamptothecin:

To a dry 100 ml round bottom flask fitted with a magnetic stir bar was added 218 mg (0.5 mmol) of 7-(1-chloropropyl) homocamptothecin and 20 ml dry dimethylsulfoxide. The mixture was allowed to stir until all the solid was dissolved. To the remaining solution was added a solution of 3 ml of 1-ethylaminopyrrolidine in 20 ml of dry toluene. The reaction mixture was allowed to stir for 4 h after which the reaction mixture was concentrated to a thick residue under high vacuum followed by purification by column chromatography using silica gel (CHCl$_3$/MeOH, 98:2 then 90:10). The evaporation of solvent gave 116 mg (45%) of 7-[3-N-(2-(1-Pyrrolidino) ethyl)aminopropyl] homocamptothecin as a yellow solid. Mp 193–195° C. (d). IR (KBr) 1660, 1765, cm$^{-1}$; $^1$H-NMR (DMSO-d$_6$) δ 0.85 (t, 3H), 1.61–1.74 (m, 6H), 1.85 (m, 2H), 2.20–2.49 (m, 6H), 2.52–2.66 (m, 6H), 3.31 (dd, 2H), 5.23 (s, 2H), 5.52 (m, 2H), 6.11 (s, 1H), 7.62 (m, 1H), 7.85 (m, 1H), 8.13 (d, 1H), 8.26 (d, 1H), 8.71 (s, 1H); $^{13}$C-NMR (DMSO-d$_6$) δ 8.50, 23.53, 33.02, 34.03, 36.45, 42.64, 48.78, 49.3, 50.78, 51.48, 55.41, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. 517.6 (C$_{30}$H$_{37}$N$_4$O$_4$).

EXAMPLE 90

7-[3-N-(4-methyl-1-piperazino)aminopropyl] homocamptothecin:

To a dry 100 ml round bottom flask fitted with a magnetic stir bar was added 218 mg (0.5 mmol) of 7-(1-chloropropyl) homocamptothecin and 20 ml dry dimethylsulfoxide. The mixture was allowed to stir until all the solid was dissolved. To the remaining solution was added a solution of 4 ml of 4-methylpiperazine in 20 ml of dry toluene. The reaction mixture was allowed to stir for 6 h after which the reaction mixture was concentrated to a thick residue under high vacuum followed by purification by column chromatography using silica gel (CHCl$_3$/MeOH, 98:2 then 90:10). The evaporation of solvent gave 124 mg (48%) of 7-[3-N-(4-methyl-1-piperazino)aminopropyl]homocamptothecin as a yellow solid. Mp 166–168° C. (d). IR (KBr) 1660, 1760, cm$^{-1}$; $^1$H-NMR (DMSO-d$_6$) δ 0.85 (t, 3H), 1.85–1.91 (m, 4H), 2.27 (s, 3H), 2.45–2.68 (m, 12H), 3.31 (dd, 2H), 5.23 (s, 2H), 5.48 (m, 2H), 6.11 (s, 1H), 7.62 (m, 1H), 7.85 (m, 1H), 8.13 (d, 1H), 8.26 (d, 1H), 8.72 (s, 1H); $^{13}$C-NMR (DMSO-d$_6$) δ 8.50, 32.10, 32.88, 36.45, 38.82, 42.64, 48.78, 50.78, 55.33, 57.34, 61.34, 73.56, 101.11, 122.59, 126.84, 128.25, 128.53, 129.21, 131.17, 131.77, 139.53, 145.21, 147.84, 152.66, 155.71, 160.18, 171.76. Anal. 518.6 (C$_{29}$H$_{36}$N$_5$O$_4$)

EXAMPLE 91

7-[5-N-(4-methyl-1-piperazino)aminopentyl] homocamptothecin:

To a dry 100 ml round bottom flask fitted with a magnetic stir bar was added 250 mg (0.5 mmol) of 7-(1-chloropentyl) camptothecin and 20 ml dry dimethylsulfoxide. The mixture was allowed to stir until all the solid was dissolved. To the remaining solution was added a solution of 4 ml of 4-methylpiperazine in 20 ml of dry toluene. The reaction mixture was allowed to stir for 5 h after which the reaction mixture was concentrated to a thick residue under high vacuum followed by purification by column chromatography using silica gel (CHCl$_3$/MeOH, 98:2 then 90:10). The evaporation of solvent gave 131 mg (48%) of 7-[5-N-(4-methyl-1-piperazino)aminopentyl] homocamptothecin as a yellow solid. Mp 201–205° C. (d). IR (KBr) 1660, 1760, cm$^{-1}$; $^1$H-NMR (DMSO-d$_6$) δ 0.85 (t, 3H), 1.29–1.65 (m, 6H), 1.85 (m, 2H), 2.26 (s, 3H), 2.45–2.68 (m, 16H), 3.31 (dd, 2H), 5.23 (s, 2H), 5.52 (m, 2H), 6.02 (s, 1H), 7.58 (m, 1H), 7.75 (m, 1H), 8.11 (d, 1H), 8.26 (d, 1H), 8.72 (s, 1H); $^{13}$C-NMR (DMSO-d$_6$) δ 8.50, 22.21, 27.22, 29.92, 33.01, 35.08, 36.45, 38.81, 42.64, 45.12, 49.21, 50.78, 55.44, 57.67, 61.34, 73.56, 101.11, 122.59, 126.84, 128.25, 128.63, 129.11, 131.17, 131.77, 139.51, 145.16, 147.84, 152.66, 155.71, 160.11, 171.78. Anal. C$_{26}$H$_{27}$ClN$_2$O$_4$ (545.6).

What is claimed is:

1. A substituted camptothecin or homocamptothecin having the structure:

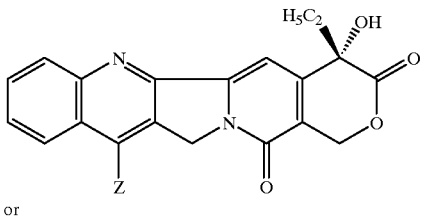

or

-continued

Where Z is:
A) $C_{1-20}$ $NR^1R^2$ where
  (1) $R^1$ is hydrogen, $C_{1-18}$ alkyl, $C_{3-7}$cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl and $R^2$ is $C_{1-20}$ $NR^3R^4$ where: (a) $R^3$ and $R^4$ are independently, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl, 3–7 membered heterocyclic ring which may contain a O, S or N group; (b) $R^3$ is hydrogen and $R^4$ is $C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$alkyl or $C_{1-18}$alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy, $C_{1-18}$ alkoxy-$C_{1-18}$ alkyl; (c) $R^3$ and $R^4$ taken together with the nitrogen atom to which they are attached form a saturated 3–7-membered heterocyclic ring which may contain a O, S or $NR^5$ group, where $R^5$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and —$COR^6$ where $R^6$ is hydrogen, $C_{1-6}$ alkyl, perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups,
  (2) $R^1$ is hydrogen, $C_{1-18}$ alkyl, $C_{3-7}$ cycloalkyl, $C_{3-7}$ cycloalkyl-$C_{1-18}$ alkyl, $C_{2-18}$alkenyl, hydroxy-$C_{1-18}$ alkyl, $C_{1-18}$ alkoxy-$C_{1-18}$ alkyl, and $R^2$ can be any one of the following alkyl polyamines:

—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(CH_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH:(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_31H(CH_2)_4NH_2$
—$(CH_2)_3NH(CH_2)_4NH(CH_2)_4NH(CH_2)_4NH_2$
—$(CH_2)_4NH(CH_2)_3NH(CH_2)_3NH(CH_2)_4NH_2$
—$(CH_2)_4NH(CH_2)_3NH(CH_2)_4NH(CH_2)_4NH_2$
—$(CH_2)_3NH(CH_2)_4NH(CH_2)_4NH(CH_2)_4NH_2$
—$(CH_2)_4NH(CH_2)_4NH(CH_2)_3NH(CH_2)_4NH_2$
—$(CH_2)_3NH(CH_2)_4NH_2)(CH_2)_4NH(CH_2)_4NH_2$
—$(CH_2)_3NH(CH_2)_3NH(CH_2)_3NH(CH_2)_3NH_2$
—$(CH_2)_3NE(CH_2)_3NH(CH_2)_3NH(CH_2)_3NH(CH_2)_4NH_2$
—$(CH_2)_3NH(CH_2)_3NH(CH_2)_3NH(CH_2)_4NH(CH_2)_3NH_2$
—$(CH_2)_3NH(CH_2)_3NH(CH_2)_4NH(CH_2)_3NH(CH_2)_3NH_2$
—$C(NH)NH(CH_2)_4NH_2$
—$C(NCH3)NH(CH_2)_4NH_2$
  (3) $R^1$ is hydrogen, $C_{1-18}$ alkyl, $C_{3-7}$ cycloalkyl, $C_{3-7}$cycloalkyl-$C_{1-18}$ alkyl, $C_{2-18}$alkenyl, hydroxy-$C_{1-18}$ alkyl, $C_{1-18}$ alkoxy-$C_{1-18}$ alkyl, and $R^2$ can be either $CO(OCH_2)_nOR^{10}$ or $CH_2$ $(OCH_2)_nOR^{10}$ where n=1–2,000 and $R^{10}$ is either hydrogen, $C_{1-10}$ alkyl, or aryl;
  (4) $NR^1R^2$ is guanidino group; and
  (5) $R^1$ is hydrogen, $C_{1-8}$ alkyl, $C_{3-7}$ cycloalkyl, $C_{3-7}$ cycloalkyl-$C_{1-8}$ alkyl, $C_{2-8}$alkenyl, hydroxy-$C_{1-8}$ alkyl, $C_{1-8}$ alkoxy-$C_{1-8}$alkyl, $R^2$ is $C_{1-8}$ alkyl-$SiR^{11}R^{12}R^{13}$ where $R^{11}$, $R^{12}$, and $R^{13}$ are methyl or $R^{11}$, $R^{12}$, and $R^{13}$ are independently $C_{1-10}$ alkyl, $C_{2-8}$ alkenyl, $C_{2-8}$ alkynyl $C_{1-8}$ alkoxy, $C_{1-8}$ aminoalkyl, $C_{1-8}$ hydroxayalkyl, and haloalkyl groups;
B) $C_{2-20}$ $NR^1R^2$ where (a) $R^1$ and $R^2$ taken together with the nitrogen atom to which they are attached form a saturated 3–7-membered heterocyclic ring which may contain a O, S or $NR^3$ group, where $R^3$ is hydrogen, $C_{1-6}$alkyl, perhalo-$C_{1-6}$ alkyl, aryl, aryl substituted with one or more groups selected from the group consisting of $C_{1-6}$ alkyl, halogen, nitro, amino, $C_{1-6}$ alkyl, $C_{1-6}$ alkoxy, $C_{1-6}$ alkoxy-$C_{1-6}$ alkyl and —$COR^4$ where $R^4$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;
C) $C_{12-20}$ $NR^1R^2$ where (1) $R^1$ and $R^2$ are independently, $C_{3-7}$ cycloalkyl, $C_{3-7}$ cycloalkyl-$C_{1-18}$ alkyl, $C_{2-18}$ alkenyl, hydroxy-$C_{1-18}$ alkyl, $C_{1-18}$ alkoxy-$C_{1-18}$ alkyl or (2) $R^1$ is hydrogen and $R^2$ is $C_{1-18}$ alkyl, $C_{3-7}$ cycloalkyl, $C_{3-7}$cycloalkyl-$C_{1-18}$ alkyl, $C_{2-8}$ alkenyl, hydroxy, $C_{1-18}$ alkyl or $C_{1-18}$ alkoxy-$C_{1-18}$ alkyl, perhalo-$C_{1-18}$ alkyl, $C_{3-7}$ cycloalkyl, $C_{3-7}$ cycloalkyl-$C_{1-18}$ alkyl, $C_{2-18}$ alkenyl, hydroxy-$C_{1-18}$alkyl, $C_{1-18}$ alkoxy, $C_{1-18}$ alkoxy-$C_{1-18}$ alkyl;
D) $NR^1R^2$ where $R^1$ is $C_{3-7}$ cycloalkyl, $C_{3-7}$ cycloalkyl-$C_{1-8}$ alkyl, $C_{2-8}$ alkenyl, hydroxy-$C_{1-8}$ alkyl, $C_{1-8}$ alkoxy-$C_{1-8}$alkyl, and $R^2$ is one of the following alkylamines or alkylpolyamines:

—$(CH_2)_3NH_2$
—$(CH_2)_4NH_2$
—$(CH_2)_5NH_2$
—$(CH_2)_3NH(CH_2)_3NH_2$
—$(CH_2)_3NH(CH_2)_4NH_2$
—$(CH_2)_3NH(CH_2)_5NH_2$
—$(CH_2)_4NH(CH_2)_4NH_2$
—$(C H_2)_3NH(CH_2)_3NH(CH_2)_3NH_2$
—$(CH_2)_3NH(CH_2)_3NH(CH_2)_4NH_2$
—$(CH_2)_3NH(CH_2)_3NH(CH_2)_5NH_2$
—$(CH_2)_3NH(CH_2)_4NH(CH_2)_3NH_2$
—$(CH_2)_3NH(CH_2)_5NH(CH_2)_3NH_2$
—$(CH_2)_3NH(CH_2)_4NH(CH_2)_4NH_2$
—$(CH_2)_4NH(CH_2)_3NH(CH_2)_4NH_2$
—$(CH_2)_4NH(CH_2)_4NH(CH_2)_4NH_2$
—$(CH_2)_3NH(CH_2)_3NH(CH_2)_3NH(CH_2)_3NH_2$
—$(CH_2)_3NH(CH_2)_4NH(CH_2)_3NH(CH_2)_4NH_2$
—$(CH_2)_3NH(CH_2)_4NH(CH_2)_4NH(CH_2)_4NH_2$

—(CH$_2$)$_4$NH(CH$_2$)$_3$NH(CH$_2$)$_3$NH(CH$_2$)$_4$NH$_2$
—(CH$_2$)$_4$NH(CH$_2$)$_3$NH(CH$_2$)$_4$NH(CH$_2$)$_4$NH$_2$
—(CH$_2$)$_3$NH(CH$_2$)$_4$NH(CH$_2$)$_4$NH(CH$_2$)$_4$NH$_2$
—(CH$_2$)$_4$NH(CH$_2$)$_4$NH(CH$_2$)$_3$NH(CH$_2$)$_4$NH$_2$
—(CH$_2$)$_3$NH(CH$_2$)$_4$NH$_2$)(CH$_2$)$_4$NH(CH$_2$)$_4$NH$_2$
—(CH$_2$)$_3$NH(CH$_2$)$_3$NH(CH$_2$)$_3$NH(CH$_2$)$_3$NH(CH$_2$)$_3$NH$_2$
—(CH$_2$)$_3$NH(CH$_2$)$_3$NH(CH$_2$)$_3$NH(CH$_2$)$_3$NH(CH$_2$)$_4$NH$_2$
—(CH$_2$)$_3$NH(CH$_2$)$_3$NH(CH$_2$)$_3$NH(CH$_2$)$_4$NH(CH$_2$)$_3$NH$_2$
—(CH$_2$)$_3$NH(CH$_2$)$_3$NH(CH$_2$)$_4$NH(CH$_2$)$_3$NH(CH$_2$)$_3$NH$_2$
—C(NH)NH(CH$_2$)$_4$NH$_2$
—C(NCH3)NH(CH$_2$)$_4$NH$_2$.

2. A pharmaceutically acceptable acid addition salt of the compound of claim 1.

* * * * *

UNITED STATES PATENT AND TRADEMARK OFFICE
CERTIFICATE OF CORRECTION

PATENT NO.   : 6,291,676 B1                                   Page 1 of 1
DATED        : September 18, 2001
INVENTOR(S)  : Thomas G. Burke, Ayhan S. Demir, Cihangir Tanyeli, Ashok J. Chavan, Tie-Lin Wang and Yves Pommier It is certified that error appears in the above-identified patent and that said Letters Patent is hereby corrected as shown below:

Column 45,
Line 56, delete ":".
Line 66, replace "$NH_2$)(" with -- $NH_2$( --

Column 46,
Line 1, replace "E" with -- H --.
Line 10, replace "$CH_2$ (OCH)" with -- $CH_2$(OCH) --.
Line 37, replace "$C_{2-8}$" with -- $C_{2-18}$ --.
Line 55, replace "(C $H_2$)" with -- ($CH_2$) --.

Column 47,
Line 6, replace "$NH_2$)(" with -- $NH_2$( --.

Signed and Sealed this

Twenty-second Day of October, 2002

Attest:

*Attesting Officer*

JAMES E. ROGAN
*Director of the United States Patent and Trademark Office*